United States Patent
Bernstein et al.

(10) Patent No.: US 12,150,982 B2
(45) Date of Patent: Nov. 26, 2024

(54) FORMULATIONS OF PBMCS

(71) Applicant: STEMCELL TECHNOLOGIES CANADA INC., Vancouver (CA)

(72) Inventors: Howard Bernstein, Cambridge, MA (US); Scott Loughhead, Watertown, MA (US); Matthew Booty, Cambridge, MA (US); Kelan Hlavaty, Belmont, MA (US); Tarek Abdeljawad, Concord, MA (US); Maisam Dadgar, Cambridge, MA (US); Jason Murray, Watertown, MA (US); David Chirgwin, Watertown, MA (US); Harry An, Watertown, MA (US); Armon R. Sharei, Somerville, MA (US)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 0 days.

(21) Appl. No.: 17/563,764

(22) Filed: Dec. 28, 2021

(65) Prior Publication Data

US 2022/0241392 A1 Aug. 4, 2022

Related U.S. Application Data

(60) Provisional application No. 63/131,454, filed on Dec. 29, 2020.

(51) Int. Cl.
| | | |
|---|---|---|
| *A61K 39/12* | (2006.01) | |
| *A61K 39/39* | (2006.01) | |
| *A61K 47/20* | (2006.01) | |
| *A61K 47/42* | (2017.01) | |
| *A61K 39/00* | (2006.01) | |

(52) U.S. Cl.
CPC .............. *A61K 39/12* (2013.01); *A61K 39/39* (2013.01); *A61K 47/20* (2013.01); *A61K 47/42* (2013.01); *A61K 2039/5154* (2013.01); *A61K 2039/55561* (2013.01)

(58) Field of Classification Search
None
See application file for complete search history.

(56) References Cited

U.S. PATENT DOCUMENTS

| | | | |
|---|---|---|---|
| 2017/0119865 A1* | 5/2017 | Lee | .................... C12N 5/0646 |
| 2018/0142198 A1 | 5/2018 | Sharei et al. | |
| 2018/0201889 A1 | 7/2018 | Sharei et al. | |
| 2022/0241392 A1* | 8/2022 | Bernstein | ................. A61K 9/19 |

FOREIGN PATENT DOCUMENTS

| | | |
|---|---|---|
| WO | WO-2013059343 A1 | 4/2013 |
| WO | WO-2015023982 A1 | 2/2015 |
| WO | WO-2016070136 A1 | 5/2016 |
| WO | WO-2017008063 A1 | 1/2017 |
| WO | WO-2017041050 A1 | 3/2017 |
| WO | WO-2017192785 A1 | 11/2017 |
| WO | WO-2017192786 A1 | 11/2017 |
| WO | WO 2018/136566 * | 7/2018 |
| WO | WO-2018136566 A1 | 7/2018 |
| WO | WO 2019/178005 * | 9/2019 |
| WO | WO-2019178005 A2 | 9/2019 |
| WO | WO-2019178006 A2 | 9/2019 |
| WO | WO-2020072833 A1 | 4/2020 |
| WO | WO-2020154696 A1 | 7/2020 |
| WO | WO 2020/176789 * | 9/2020 |
| WO | WO-2020176789 A1 | 9/2020 |
| WO | WO-2022147017 A1 | 7/2022 |

OTHER PUBLICATIONS

Ma et al. (Acta Biomaterialia. 2021; 131: 97-116).*
International Search Report and Written Opinion for International Application No. PCT/US2021/065352, mailed on Apr. 7, 2022, European Patent Office, Netherlands, 11 pages.
Li, R., et al., "Preservation of cell-based immunotherapies for clinical trials," Cytotherapy 21(9):943-957, Elsevier, Netherlands (2019).
Papaioannou, N.E., et al., "Harnessing the immune system to improve cancer therapy" Ann. Trans. Med. 4(14):261, AME Publishing Company, China (2016).
Suresh, T., and Burtness, B., "The emerging role of immunotherapy in head and neck squamous cell cancer," Am. J. Hematol. Oncol. 13(6):20-27, Wiley, United States (2017).

* cited by examiner

*Primary Examiner* — Shanon A. Foley
(74) *Attorney, Agent, or Firm* — BERESKIN & PARR LLP/S.E.N.C.R.L., s.r.l.; Micheline Gravelle

(57) ABSTRACT

The present application provides formulations of modified peripheral blood mononuclear cells (PBMCs), wherein the formulation comprises: PBMCs comprising at least one antigen (e.g., a human papillomavirus (HPV) antigen) and a cryopreservation medium. In some embodiments, the PBMCs are conditioned by incubating the PBMC in the presence of an adjuvant.

18 Claims, No Drawings

Specification includes a Sequence Listing.

SEQUENCE LISTING

<160> NUMBER OF SEQ ID NOS: 50

<210> SEQ ID NO 1
<211> LENGTH: 10
<212> TYPE: PRT
<213> ORGANISM: Human papilloma virus

```
<400> SEQUENCE: 1

Thr Ile His Asp Ile Ile Leu Glu Cys Val
1               5                   10

<210> SEQ ID NO 2
<211> LENGTH: 10
<212> TYPE: PRT
<213> ORGANISM: Human papilloma virus

<400> SEQUENCE: 2

Glu Val Tyr Asp Phe Ala Phe Arg Asp Leu
1               5                   10

<210> SEQ ID NO 3
<211> LENGTH: 10
<212> TYPE: PRT
<213> ORGANISM: Human papilloma virus

<400> SEQUENCE: 3

Tyr Met Leu Asp Leu Gln Pro Glu Thr Thr
1               5                   10

<210> SEQ ID NO 4
<211> LENGTH: 9
<212> TYPE: PRT
<213> ORGANISM: Human papilloma virus

<400> SEQUENCE: 4

Arg Ala His Tyr Asn Ile Val Thr Phe
1               5

<210> SEQ ID NO 5
<211> LENGTH: 10
<212> TYPE: PRT
<213> ORGANISM: Human papilloma virus

<400> SEQUENCE: 5

Leu Pro Gln Leu Ser Thr Glu Leu Gln Thr
1               5                   10

<210> SEQ ID NO 6
<211> LENGTH: 8
<212> TYPE: PRT
<213> ORGANISM: Human papilloma virus

<400> SEQUENCE: 6

Gln Leu Cys Thr Glu Leu Gln Thr
1               5

<210> SEQ ID NO 7
<211> LENGTH: 7
<212> TYPE: PRT
<213> ORGANISM: Human papilloma virus

<400> SEQUENCE: 7

Lys Gln Gln Leu Leu Arg Arg
1               5

<210> SEQ ID NO 8
<211> LENGTH: 10
<212> TYPE: PRT
<213> ORGANISM: Human papilloma virus

<400> SEQUENCE: 8
```

Val Tyr Ser Lys Gln Gln Leu Leu Arg Arg
1               5                   10

<210> SEQ ID NO 9
<211> LENGTH: 10
<212> TYPE: PRT
<213> ORGANISM: Human papilloma virus

<400> SEQUENCE: 9

Met His Gly Asp Thr Pro Thr Leu His Glu
1               5                   10

<210> SEQ ID NO 10
<211> LENGTH: 6
<212> TYPE: PRT
<213> ORGANISM: Human papilloma virus

<400> SEQUENCE: 10

Gly Gln Ala Glu Pro Asp
1               5

<210> SEQ ID NO 11
<211> LENGTH: 16
<212> TYPE: PRT
<213> ORGANISM: Human papilloma virus

<400> SEQUENCE: 11

Tyr Ser Lys Gln Gln Leu Leu Arg Arg Glu Val Tyr Asp Phe Ala Phe
1               5                   10                  15

<210> SEQ ID NO 12
<211> LENGTH: 7
<212> TYPE: PRT
<213> ORGANISM: Human papilloma virus

<400> SEQUENCE: 12

Tyr Cys Lys Gln Gln Leu Leu
1               5

<210> SEQ ID NO 13
<211> LENGTH: 8
<212> TYPE: PRT
<213> ORGANISM: Human papilloma virus

<400> SEQUENCE: 13

Cys Ile Val Tyr Arg Asp Gly Asn
1               5

<210> SEQ ID NO 14
<211> LENGTH: 15
<212> TYPE: PRT
<213> ORGANISM: Human papilloma virus

<400> SEQUENCE: 14

Ser Ile Val Tyr Arg Asp Gly Asn Pro Tyr Ala Val Ser Asp Lys
1               5                   10                  15

<210> SEQ ID NO 15
<211> LENGTH: 15
<212> TYPE: PRT
<213> ORGANISM: Human papilloma virus

<400> SEQUENCE: 15

Asp Leu Tyr Cys Tyr Glu Gln Leu Asn Asp Ser Ser Glu Glu Glu
1               5                   10                  15

<210> SEQ ID NO 16
<211> LENGTH: 20
<212> TYPE: PRT
<213> ORGANISM: Human papilloma virus

<400> SEQUENCE: 16

Cys Cys Lys Cys Asp Ser Thr Leu Arg Leu Cys Val Gln Ser Thr His
1               5                   10                  15

Val Asp Ile Arg
            20

<210> SEQ ID NO 17
<211> LENGTH: 20
<212> TYPE: PRT
<213> ORGANISM: Human papilloma virus

<400> SEQUENCE: 17

Ser Ser Lys Ser Asp Ser Thr Leu Arg Leu Ser Val Gln Ser Thr His
1               5                   10                  15

Val Asp Ile Arg
            20

<210> SEQ ID NO 18
<211> LENGTH: 36
<212> TYPE: PRT
<213> ORGANISM: Artificial Sequence
<220> FEATURE:
<223> OTHER INFORMATION: Synthetic Construct

<400> SEQUENCE: 18

Leu Pro Gln Leu Ser Thr Glu Leu Gln Thr Thr Ile His Asp Ile Ile
1               5                   10                  15

Leu Glu Cys Val Tyr Ser Lys Gln Gln Leu Leu Arg Arg Glu Val Tyr
                20                  25                  30

Asp Phe Ala Phe
            35

<210> SEQ ID NO 19
<211> LENGTH: 25
<212> TYPE: PRT
<213> ORGANISM: Artificial Sequence
<220> FEATURE:
<223> OTHER INFORMATION: Synthetic Construct

<400> SEQUENCE: 19

Gln Leu Cys Thr Glu Leu Gln Thr Thr Ile His Asp Ile Ile Leu Glu
1               5                   10                  15

Cys Val Tyr Cys Lys Gln Gln Leu Leu
                20                  25

<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Lys Gln Gln Leu Leu Arg Arg Glu Val Tyr Asp Phe Ala Phe Arg Asp
1               5                   10                  15

Leu Cys Ile Val Tyr Arg Asp Gly Asn
                20                  25

```
<210> SEQ ID NO 21
<211> LENGTH: 35
<212> TYPE: PRT
<213> ORGANISM: Artificial Sequence
<220> FEATURE:
<223> OTHER INFORMATION: Synthetic Construct

<400> SEQUENCE: 21

Val Tyr Ser Lys Gln Gln Leu Leu Arg Arg Glu Val Tyr Asp Phe Ala
1               5                   10                  15

Phe Arg Asp Leu Ser Ile Val Tyr Arg Asp Gly Asn Pro Tyr Ala Val
                20                  25                  30

Ser Asp Lys
        35

<210> SEQ ID NO 22
<211> LENGTH: 35
<212> TYPE: PRT
<213> ORGANISM: Artificial Sequence
<220> FEATURE:
<223> OTHER INFORMATION: Synthetic Construct

<400> SEQUENCE: 22

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu
        35

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Gln Leu Cys Thr Glu Leu Gln Thr Tyr Met Leu Asp Leu Gln Pro Glu
1               5                   10                  15

Thr Thr Tyr Cys Lys Gln Gln Leu Leu
                20                  25

<210> SEQ ID NO 24
<211> LENGTH: 35
<212> TYPE: PRT
<213> ORGANISM: Artificial Sequence
<220> FEATURE:
<223> OTHER INFORMATION: Synthetic Construct

<400> SEQUENCE: 24

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
                20                  25                  30

Asp Ile Arg
        35

<210> SEQ ID NO 25
<211> LENGTH: 35
<212> TYPE: PRT
<213> ORGANISM: Artificial Sequence
```

<220> FEATURE:
<223> OTHER INFORMATION: Synthetic Construct

<400> SEQUENCE: 25

Gly Gln Ala Glu Pro Asp Arg Ala His Tyr Asn Ile Val Thr Phe Ser
1               5                   10                  15
Ser Lys Ser Asp Ser Thr Leu Arg Leu Ser Val Gln Ser Thr His Val
            20                  25                  30
Asp Ile Arg
        35

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ggggtcaacg ttgagggggg                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
gggggacgat cgtcgggggg                                           20

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
ggggacgacg tcgtggggg g                                          21

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
tccatgacgt tcctgatgct                                           20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
tccatgacgt tcctgacgtt                                           20

<210> SEQ ID NO 31
<211> LENGTH: 24
<212> TYPE: DNA
<213> ORGANISM: Artificial Sequence

```
<220> FEATURE:
<223> OTHER INFORMATION: Synthetic Construct

<400> SEQUENCE: 31
tcgtcgtttt gtcgttttgt cgtt                                          24

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
tcgtcgttgt cgttttgtcg tt                                            22

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
tcgacgttcg tcgttcgtcg ttc                                           23

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
tcgcgacgtt cgcccgacgt tcggta                                        26

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
tcgtcgtttt cggcgcgcgc cg                                            22

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
tcgtcgtcgt tcgaacgacg ttgat                                         25

<210> SEQ ID NO 37
<211> LENGTH: 29
<212> TYPE: DNA
<213> ORGANISM: Artificial Sequence
<220> FEATURE:
<223> OTHER INFORMATION: Synthetic Construct

<400> SEQUENCE: 37
tcgcgaacgt tcgccgcgtt cgaacgcgg                                     29
```

<210> SEQ ID NO 38
<211> LENGTH: 35
<212> TYPE: PRT
<213> ORGANISM: Artificial Sequence
<220> FEATURE:
<223> OTHER INFORMATION: Synthetic Construct

<400> SEQUENCE: 38

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct

<400> SEQUENCE: 39

Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct

<400> SEQUENCE: 40

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct

<400> SEQUENCE: 41

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35

<210> SEQ ID NO 42
<211> LENGTH: 32

<212> TYPE: PRT
<213> ORGANISM: Artificial Sequence
<220> FEATURE:
<223> OTHER INFORMATION: Synthetic Construct

<400> SEQUENCE: 42

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

Leu Pro Gln Leu Cys Thr Glu Leu Gln Thr Thr Ile His Asp Ile Ile
1               5                   10                  15

Leu Glu Cys Val Tyr Cys Lys Gln Gln Leu Leu Arg Arg Glu Val Tyr
            20                  25                  30

<210> SEQ ID NO 44
<211> LENGTH: 25
<212> TYPE: PRT
<213> ORGANISM: Artificial Sequence
<220> FEATURE:
<223> OTHER INFORMATION: Synthetic Construct

<400> SEQUENCE: 44

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct

<400> SEQUENCE: 45

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

<400> SEQUENCE: 46

Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25

<210> SEQ ID NO 47

```
<211> LENGTH: 25
<212> TYPE: PRT
<213> ORGANISM: Artificial Sequence
<220> FEATURE:
<223> OTHER INFORMATION: Synthetic Construct

<400> SEQUENCE: 47

His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25

<210> SEQ ID NO 48
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct

<400> SEQUENCE: 49

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30
```

FORMULATIONS OF PBMCS

CROSS REFERENCE TO RELATED APPLICATIONS

This application claims the benefit of U.S. Provisional Application No. 63/131,454, filed on Dec. 29, 2020, the entire contents of which are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322003000SEQLIST.TXT, date recorded: Dec. 23, 2021, size: 12,994 bytes).

FIELD OF THE INVENTION

The present disclosure relates generally to formulations of peripheral blood mononuclear cells (PBMCs) comprising at least one antigen in a cryopreservation medium. Also provided are methods of manufacturing such PBMCs comprising the at least one antigen, methods of formulating the cryopreservable formulation, and methods of cryopreserving the formulation.

BACKGROUND OF THE INVENTION

Papillomaviruses are small nonenveloped DNA viruses with a virion size of ~55 nm in diameter. More than 100 human papilloma virus (HPV) genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN).

Many of the known HPV types cause benign lesions with a subset being oncogenic. Based on epidemiologic and phylogenetic relationships, HPV types are classified into fifteen "high-risk types" (HPV 16, 18, 31, 33, 35, 39, 45, 51, 52, 56, 58, 59, 68, 73, and 82) and three "probable high-risk types" (HPV 26, 53, and 66), which together are known to manifest as low and high grade cervical changes and cancers, as well as other anogential cancers such as vulval, vaginal, penile, anal, and perianal cancer, as well as head and neck cancers. Recently, the association of high-risk types HPV 16 and 18 with breast cancer was also described. Eleven HPV types classified as "low-risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness *Am J Hematol Oncol* 13(6):20-27 (2017).

Immunotherapy can be divided generally into two main types of interventions, either passive or active. Passive protocols include administration of pre-activated and/or engineered cells (e.g., CAR T cells), disease-specific therapeutic antibodies, and/or cytokines. Active immunotherapy strategies are directed at stimulating immune system effector functions in vivo. Several current active protocols include vaccination strategies with disease-associated peptides, lysates, or allogeneic whole cells, infusion of autologous dendritic cell (DCs) as vehicles for tumor antigen delivery, and infusion of immune checkpoint modulators. See Papaioannou, Nikos E., et al. *Annals of translational medicine* 4.14 (2016). Adoptive immunotherapy can be employed to modulate the immune response, enhance antitumor activity, and achieve the goal of treating or preventing HPV-associated cancers.

$CD8^+$ cytotoxic T lymphocytes (CTL) and $CD4^+$ helper T (Th) cells stimulated by disease-associated antigens have the potential to target and destroy diseased cells; however, current methods for inducing endogenous T cell responses have faced challenges. The methods described herein are used to efficiently generate PBMCs comprising at least one antigen in a high throughput manner, which can be utilized in inducing a robust antigen-specific T cell response. Disclosed are formulations of PBMCs comprising at least one antigen, a cryopreservation medium, and one/or more agents that enhance the viability and/or function of PBMCs. Also disclosed are methods of manufacturing such PBMCs comprising the at least one antigen, methods of formulating the cryopreservable formulation, and methods of cryopreserving the formulation The methods described herein also describe methods, treatments, doses and regimens for treating individuals with HPV-associated cancers using PBMCs comprising HPV antigens and/or adjuvants.

All references cited herein, including patent applications and publications, are incorporated by reference in their entirety. The patent publications WO 2013/059343, WO 2015/023982, WO 2016/070136, WO2017041050, WO2017008063, WO 2017/192785, WO 2017/192786, WO 2019/178005, WO 2019/178006, WO 2020/072833, WO 2020/154696, and WO 2020/176789, US 20180142198, and US 20180201889 are hereby expressly incorporated by reference in their entirety.

BRIEF SUMMARY OF THE INVENTION

In some aspects, the invention provides a pharmaceutical formulation comprising peripheral blood mononuclear cells (PBMCs), the formulation comprising a) PBMCs wherein the PBMCs comprise at least one antigen, b) a cryopreservation medium, and c) human serum albumin. In some aspects, the invention provides a pharmaceutical formulation comprising peripheral blood mononuclear cells (PBMCs), the formulation comprising a) PBMCs wherein the PBMCs comprise at least one antigen, b) a cryopreservation medium, c) a hypothermic preservation medium, and d) human serum albumin. In some embodiments, the composition comprises about $5 \times 10^6$ PBMCs to about $5 \times 10^7$ PBMC. In some embodiments, the composition comprises about $2 \times 10^7$ PBMCs to about $3 \times 10^7$ PBMCs. In some embodiments, the composition comprises about $2.75 \times 10^7$ PBMCs. In some embodiments, the composition comprises about $1 \times 10^6$ PBMCs/mL to about $1 \times 10^7$ PBMC/mL. In some embodiments, the composition comprises about $4 \times 10^6$ PBMCs/mL to about $6 \times 10^6$ PBMCs/mL. In some embodiments, the composition comprises about $5.0 \times 10^6$ PBMCs/mL. In some embodiments, ≥70%, ≥80%, ≥90%, or ≥95% of the PBMCs in the composition are viable. In some embodiments, the composition comprises about $3\times10^6$ viable PBMCs/mL to about $7\times10^6$ viable PBMCs/mL. In some embodiments, the composition comprises about $5\times10^6$ viable PBMCs/mL. In some embodiments, the composition had previously been frozen and the composition comprises about $4\times10^6$ viable PBMCs/mL after thawing. In some embodiments, the PBMCs in the formulation maintain about ≥70% viability following storage for at least about 12 months at ≤−196° C.

In some embodiments, the percentage of the cryopreservation medium in the formulation is about 40% to about 95% (w/w). In some embodiments, the percentage of the cryopreservation medium in the formulation is about 80% (w/w). In some embodiments, the percentage of the cryopreservation medium in the formulation is about 50% (w/w). In some embodiments, the cryopreservation medium comprises dimethylsulfoxide (DMSO). In some embodiments, the percentage of DMSO is the cryopreservation medium is about 5% to about 15% (w/w). In some embodiments, the percentage of DMSO is the cryopreservation medium is about 10% DMSO (w/w). In some embodiments, the cryopreservation medium is CryoStor® CS10.

In some embodiments, the percentage of hypothermic preservation medium in the formulation is about 25% to about 35% (w/w). In some embodiments, the percentage of the hypothermic preservation medium in the formulation is about 30% (w/w). In some embodiments, the hypothermic preservation medium comprises a water soluble analog of vitamin E. In some embodiments, the hypothermic medium comprises trolox ((±)-6-hydroxy-2,5,7,8-tetramethylchromane-2-carboxylic acid). In some embodiments, the hypothermic preservation medium is HypoThermasol® FRS.

In some embodiments, the human serum albumin is provided in a human serum albumin solution. In some embodiments, the percentage of a human serum albumin solution in the formulation is about 15% to about 25% (w/w). In some embodiments, the percentage of a human serum albumin solution in the formulation is about is about 20% (w/w). In some embodiments, the human serum albumin solution comprises sodium caprylate at a concentration of about 0.08 mmol/g of albumin and/or acetyltryptophan at a concentration of about 0.08 mmol/g albumin. In some embodiments, the percentage of a human serum albumin in the formulation is about is about 2% to about 8% (w/w). In some embodiments, the percentage of a human serum albumin in the formulation is about is about 5% (w/w).

In some embodiments, the pH of the formulation is about 6.0 to about 8.5. In some embodiments, the pH of the formulation is about 7.4.

In some aspects, the invention provides a pharmaceutical formulation of peripheral blood mononuclear cells (PBMCs), the formulation comprising a) about $1\times10^6$ PBMCs/mL to about $1\times10^7$ PBMCs/mL, wherein PBMCs comprise at least one antigen, b) cryopreservation medium at a percentage of about 65% to about 95% (w/w), and c) human serum albumin about 2% to about 8%, wherein the pH of the formulation is about pH 6.0 to about pH 8.5. In some aspects, the invention provides a pharmaceutical formulation of peripheral blood mononuclear cells (PBMCs), the formulation comprising a) about $5\times10^6$ PBMCs/mL, wherein PBMCs comprise at least one antigen, b) cryopreservation medium at a percentage of about 50% (w/w), and c) human serum albumin at a percentage of about 5% (w/w), wherein the pH of the formulation is about pH 7.4. In some aspects, the invention provides a pharmaceutical formulation of peripheral blood mononuclear cells (PBMCs), the formulation comprising a) about $1\times10^6$ PBMCs/mL to about $1\times10^7$ PBMCs/mL, wherein PBMCs comprise at least one antigen, b) cryopreservation medium at a percentage of about 40% to about 60% (w/w), c) hypothermic preservation medium at a percentage of about 25% to about 35%, and d) human serum albumin about 2% to about 8%, wherein the pH of the formulation is about pH 6.0 to about pH 8.5. In some aspects, the invention provides a pharmaceutical formulation of peripheral blood mononuclear cells (PBMCs), the formulation comprising a) about $5\times10^6$ PBMCs/mL, wherein PBMCs comprise at least one antigen, b) cryopreservation medium at a percentage of about 50% (w/w), c) hypothermic preservation medium at a percentage of about 30% (w/w), and d) human serum albumin at a percentage of about 5% (w/w), wherein the pH of the formulation is about pH 7.4. In some embodiments, the cryopreservation medium is CryoStor® CS10. In some embodiments, the hypothermic preservation medium is HypoThermasol® FRS.

In some embodiments, the formulation of the invention is sterile. In some embodiments, the formulation comprises less than about 2 EU/mL endotoxin. In some embodiments, the formulation is free of mycoplasma.

In some embodiments of the invention, the PBMCs comprises two or more of T cells, B cells, NK cells or monocytes. In some embodiments, the PBMCs comprises T cells, B cells, NK cells and monocytes. In some embodiments, (a) about 25% to about 80% of the PBMCs are T cells; (b) about 1.5% to about 30% of the PBMCs are B cells; (c) about 3.0% to about 20% of the PBMCs are NK cells; or (d) about 4.0% to about 45% of the PBMCs are monocytes.

In some embodiments of the invention, the at least one antigen is a human papillomavirus (HPV) antigen. In some embodiments, the HPV is HPV-16 or HPV-18. In some embodiments, the at least one antigen comprises a peptide derived from HPV E6 and/or E7. In some embodiments, the at least one antigen comprises a peptide derived from HPV E6 and a peptide from HPV E7. In some embodiments, the at least one antigen comprises the amino acid sequence of any one of SEQ ID NOs:1-3. In some embodiments, the at least one antigen comprises the amino acid sequence of any one of SEQ ID NOs: 18-25. In some embodiments, the population of PBMCs comprises an antigen comprising the amino acid sequence of SEQ ID NO:19 and an antigen comprising the amino acid sequence of SEQ ID NO:23.

In some embodiments of the invention, the PBMCs comprising the at least one antigen are prepared by a process comprising: a) passing a cell suspension comprising a population of input PBMCs through a cell-deforming constriction, wherein a diameter of the constriction is a function of a diameter of the input PBMCs in the suspension, thereby causing perturbations of the input PBMCs large enough for the at least one antigen to pass through to form a population of perturbed input PBMCs; and b) incubating the population of perturbed input PBMCs with the at least one antigen for a sufficient time to allow the antigen to enter the perturbed input PBMCs, thereby generating the population of PBMCs comprising the at least one antigen. In some embodiments, the diameter of the constriction is about 4.2 µm to about 6 µm or about 4.2 µm to about 4.8 µm. In some embodiments, the PBMCs comprising the at least one antigen are conditioned. In some embodiments, the population of PBMCs comprising the at least one antigen are conditioned by a process comprising incubating the PBMCs with the adjuvant for about 2 hours to about 10 hours, about 3 hours to about 6 hours, or about 4 hours at about 37° C. for the modified PBMCs to condition. In some embodiments, the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist. In some embodiments, the adjuvant is a CpG 7909 oligodeoxynucleotide (ODN).

In some aspects, the invention provides a vial comprising a formulation, the formulation comprising a) about $5 \times 10^6$ PBMCs to about $5 \times 10^7$ PBMCs, wherein PBMCs comprise at least one antigen, b) cryopreservation medium at a concentration of about 65% to about 95% (w/w), and c) human serum albumin about 2% to about 8% (w/w), wherein the pH of the formulation is about pH 6.0 to about pH 8.5. In some aspects, the invention provides a vial comprising a formulation, the formulation comprising a) about $2.75 \times 10^7$ PBMCs, wherein PBMCs comprise at least one antigen, b) cryopreservation medium at a concentration of about 80% (w/w), and c) human serum albumin at a concentration of about 5%, wherein the pH of the formulation is about pH 7.4. In some aspects, the invention provides a vial comprising a formulation, the formulation comprising a) about $1 \times 10^6$ PBMCs/mL to about $1 \times 10^7$ PBMCs/mL, wherein PBMCs comprise at least one antigen, b) cryopreservation medium at a concentration of about 40% to about 60% (w/w), c) hypothermic preservation medium about 25% to about 35% (w/w), and d) human serum albumin about 2% to about 8%, wherein the pH of the formulation is about pH 6.0 to about pH 8.5. In some aspects, the invention provides a vial comprising a formulation, the formulation comprising a) about $5 \times 10^6$ PBMCs/mL, wherein PBMCs comprise at least one antigen, b) cryopreservation medium at a concentration of about 50% (w/w), c) hypothermic preservation medium at a concentration of about 30% (w/w), and d) human serum albumin at a concentration of about 5% (w/w), wherein the pH of the formulation is about pH 7.4. In some embodiments, the cryopreservation medium is CryoStor® CS10. In some embodiments, the hypothermic preservation medium is HypoThermasol® FRS. In some embodiments, the formulation is sterile.

In some aspects, the invention provides a method of producing a formulation of PBMCs, the method comprising adding a cryopreservation medium and human serum albumin to a population of PBMCs wherein the PBMCs comprise at least one antigen. In some embodiments, a) the population of PBMCs in the formulation is about $1 \times 10^6$ PBMCs/mL to about $1 \times 10^7$ PBMCs/mL, b) the cryopreservation medium is added to a percentage of about 65% to about 95% (w/w), and c) the human serum albumin is added to a concentration of about 2% to about 8% (w/w), wherein the pH of the formulation is adjusted to about pH 6.0 to about pH 8.5. In some embodiments, a) the population of PBMCs in the formulation is about $6 \times 10^6$ PBMCs, b) the cryopreservation medium is added to a percentage of about 80% (w/w), and c) the human serum albumin is added to a percentage of about 5% (w/w), wherein the pH of the formulation is adjusted to about pH 7.4.

In some aspects, the invention provides a method of producing a formulation of PBMCs, the method comprising adding a cryopreservation medium, a hypothermic preservation medium, and human serum albumin solution to a population of PBMCs wherein the PBMCs comprise an antigen. In some embodiments, a) the population of PBMCs in the formulation is about $1 \times 10^6$ PBMCs to about $1 \times 10^7$ PBMCs, b) the cryopreservation medium is added to a percentage of about 40% to about 60% (w/w), c) the hypothermic preservation medium is added to a percentage of about 25% to about 35% (w/w), and d) the human serum albumin solution is added to a percentage of about 15% to about 25% (w/w), wherein the pH of the formulation is adjusted to about pH 6.0 to about pH 8.5. In some embodiments, a) the population of PBMCs in the formulation is about $6 \times 10^6$ PBMCs, b) the cryopreservation medium is added to a percentage of about 50% (w/w), c) the hypothermic preservation medium is added to a percentage of about 30% (w/w), and d) the human serum albumin is added to a percentage of about 20% (w/w), wherein the pH of the formulation is adjusted to about pH 7.4.

In some embodiments, the cryopreservation medium is CryoStor® CS10. In some embodiments, the hypothermic preservation medium is HypoThermasol® FRS.

DETAILED DESCRIPTION OF THE INVENTION

In some aspects, the present invention provides a pharmaceutical formulation comprising peripheral blood mononuclear cells (PBMCs), the formulation comprising PBMCs wherein the PBMCs comprise at least one antigen, a cryopreservation medium, and human serum albumin. In some aspects, the present invention provides a pharmaceutical formulation comprising PBMCs, the formulation comprising PBMCs wherein the PBMCs comprise at least one antigen, a cryopreservation medium, a hypothermic preservation medium, and human serum albumin. Also provided are vials comprising the formulation described herein.

In some aspects, the present invention provides a pharmaceutical formulation of PBMCs, the formulation comprising about $1 \times 10^6$ PBMCs/mL to about $1 \times 10^7$ PBMCs/mL, wherein PBMCs comprise at least one antigen, cryopreservation medium at a percentage of about 65% to about 95% (w/w), and human serum albumin about 2% to about 8%, wherein the pH of the formulation is about pH 6.0 to about pH 8.5. Also provided are vials comprising the formulation described herein.

In some aspects, the present invention provides a pharmaceutical formulation of PBMCs, the formulation comprising about $1 \times 10^6$ PBMCs/mL to about $1 \times 10^7$ PBMCs/mL, wherein PBMCs comprise at least one antigen, cryopreservation medium at a percentage of about 40% to about 60% (w/w), hypothermic preservation medium at a percentage of about 25% to about 35%, and human serum albumin about 2% to about 8%, wherein the pH of the formulation is about pH 6.0 to about pH 8.5. Also provided are vials comprising the formulation described herein.

In some aspects, the present invention provides a vial comprising a pharmaceutical formulation; the pharmaceutical formulation comprising about $1 \times 10^6$ PBMCs/mL to about $1 \times 10^7$ PBMCs/mL in a cryopreservation medium (such as but not limited to CryoStor® CS10) and/or one or more agents that enhance the viability and/or function of PBMCs, wherein the PBMCs comprise at least one antigen, wherein the pH of the formulation is about pH 7.4.

In some aspects, the present invention provides a vial comprising a pharmaceutical formulation; the pharmaceutical formulation comprising about $4 \times 10^6$ PBMCs/mL to about $5 \times 10^6$ PBMCs/mL in a cryopreservation medium (such as but not limited to CryoStor® CS10) and/or one or more agents that enhance the viability and/or function of PBMCs, wherein the PBMCs comprise at least one antigen, wherein the pH of the formulation is about pH 7.4.

Also provided are formulations and vials comprising PBMCs comprising at least one antigen, and the methods of preparing the formulation of PBMCS comprising at least one antigen. In some embodiments, the AACs are prepared by a process comprising: a) passing a cell suspension comprising a population of input PBMCs through a cell-deforming constriction, wherein a diameter of the constriction is a function of a diameter of the input PBMCs in the suspension, thereby causing perturbations of the input PBMCs large enough for the at least one antigen to pass through to form a population of perturbed input PBMCs; and b) incubating the population of perturbed input PBMCs with the at least one antigen for a sufficient time to allow the antigen to enter the perturbed input PBMCs, thereby generating the population of PBMCs comprising the at least one antigen. In some embodiments, the antigen is a HPV antigen. Also provided are compositions for use in inducing an immune response to HPV antigens or for treating a HPV-associated cancer. Also provided are uses of the formulation comprising an effective amount of the PBMCs in the manufacture of a medicament for stimulating an immune response to a HPV antigen or for treating a HPV-associated cancer.

In some embodiments, provided are methods of producing any of the formulations of PBMCs described herein, the method comprising adding a cryopreservation medium, a hypothermic preservation medium and/or human serum albumin to a population of PBMCs wherein the PBMCs comprise at least one antigen.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., 4th ed., Cold Spring Harbor Laboratory Press, Cold Spring Harbor, N. Y., 2012); *Current Protocols in Molecular Biology* (F. M. Ausubel, et al. eds., 2003); the series *Methods in Enzymology* (Academic Press, Inc.); *PCR 2: A Practical Approach*(M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications*(R. I. Freshney, 6th ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies*(M. Zanetti and J. D. Capra, eds., Harwood Academic Publishers, 1995); and *Cancer: Principles and Practice of Oncology* (V. T. DeVita et al., eds., J. B. Lippincott Company, 2011)

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

The terms "comprising," "having," "containing," and "including," and other similar forms, and grammatical equivalents thereof, as used herein, are intended to be equivalent in meaning and to be open ended in that an item or items following any one of these words is not meant to be an exhaustive listing of such item or items, or meant to be limited to only the listed item or items. For example, an article "comprising" components A, B, and C can consist of (i.e., contain only) components A, B, and C, or can contain not only components A, B, and C but also one or more other components. As such, it is intended and understood that "comprises" and similar forms thereof, and grammatical equivalents thereof, include disclosure of embodiments of "consisting essentially of" or "consisting of."

Where a range of values is provided, it is understood that each intervening value, to the tenth of the unit of the lower limit, unless the context clearly dictates otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a "peripheral blood mononuclear cells" or "PBMCs" refers to a heterogeneous population of blood cells having a round nucleus. Examples of cells that may be found in a population of PBMCs include lymphocytes such as T cells, B cells, NK cells (including natural killer T cells (NKT cells) and cytokine-induced killer cells (CIK cells)) and monocytes such as macrophages and dendritic cells. A "plurality of PBMCs" as used herein refers to a preparation of PBMCs comprising cells of at least two types of blood cells. In some embodiments, a plurality of PBMCs comprises two or more of T cells, B cells, NK cells, macrophages or dendritic cells. In some embodiments, a plurality of PBMCs comprises three or more of T cells, B cells, NK cells, macrophages or dendritic cells. In some embodiments, a plurality of PBMCs comprises four or more of T cells, B cells, NK cells, macrophages or dendritic cells. In some embodiments, a plurality of PBMCs comprises T cells, B cells, NK cells, macrophages and dendritic cells.

PBMCs can be isolated by means known in the art. For example, PBMCs can be derived from peripheral blood of an individual based on density of PBMCs compared to other blood cells. In some embodiments, PBMCs are derived from peripheral blood of an individual using Ficoll (e.g., a ficoll gradient). In some embodiments, PBMCs are derived from peripheral blood of an individual using ELUTRA® cell separation system. PBMCs can be obtained from an individual undergoing apheresis.

In some embodiments, a population of PBMCs is isolated from an individual. In some embodiments, a plurality of PBMCs is an autologous population of PBMCs where the population is derived from a particular individual, manipulated by any of the methods described herein, and returned to the particular individual. In some embodiments, a plurality of PBMCs is an allogeneic population of PBMCs where the population is derived from one individual, manipulated by any of the methods described herein, and administered to a second individual.

In some embodiments, a plurality of PBMCs is a reconstituted preparation of PBMCs. In some embodiments, the plurality of PBMCs may be generated by mixing cells typically found in a population of PBMCs; for example, by mixing populations of two or more of T cells, B cells, NK cells, or monocytes.

As used herein "payload" refers to the material that is being delivered into, such as loaded in, the PBMCs. "Payload," "cargo," "delivery material," and "compound" are used interchangeably herein as they refer to material that is being delivered into a cell. In some embodiments, a payload may refer to a protein, a small molecule, a nucleic acid (e.g., RNA and/or DNA), a lipid, a carbohydrate, a macromolecule, a vitamin, a polymer, fluorescent dyes and fluorophores, carbon nanotubes, quantum dots, nanoparticles, and steroids. In some embodiments, the payload may refer to a protein or small molecule drug. In some embodiments, the payload may comprise one or more compounds.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

The term "exogenous" when used in reference to an agent, such as an antigen or an adjuvant, with relation to a cell refers to an agent outside of the cell or an agent delivered into the cell from outside the cell. The cell may or may not have the agent already present, and may or may not produce the agent after the exogenous agent has been delivered.

The term "homologous" as used herein refers to a molecule which is derived from the same organism. In some examples the term refers to a nucleic acid or protein which is normally found or expressed within the given organism.

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of cancer (such as, for example, tumor volume). The methods of the invention contemplate any one or more of these aspects of treatment.

As used herein, the term "prophylactic treatment" refers to treatment, wherein an individual is known or suspected to have or be at risk for having a disorder but has displayed no symptoms or minimal symptoms of the disorder. An individual undergoing prophylactic treatment may be treated prior to onset of symptoms. In some embodiments, an individual may be treated if they have a precancerous lesion, particularly a precancerous lesion associated with HPV infection.

As used herein, by "combination therapy" is meant that a first agent be administered in conjunction with another agent. "In conjunction with" refers to administration of one treatment modality in addition to another treatment modality, such as administration of a composition of PBMCs as described herein in addition to administration of an immunoconjugate as described herein to the same individual. As such, "in conjunction with" refers to administration of one treatment modality before, during, or after delivery of the other treatment modality to the individual.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

In the context of cancer, the term "treating" includes any or all of killing cancer cells, inhibiting growth of cancer cells, inhibiting replication of cancer cells, lessening of overall tumor burden and ameliorating one or more symptoms associated with the disease.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In some examples, "modulate" refers to enhancing the presence or activity of a particular target. In some examples, "modulate" refers to suppressing the presence or activity of a particular target. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, gene editing and so forth. In other examples, inhibition of the expression of a protein may include, but not be limited to, reduction in the transcription of a nucleic acid encoding the protein, reduction in the stability of mRNA encoding the protein, inhibition of translation of the protein, reduction in stability of the protein, and so forth. In another example, inhibit may refer to the act of slowing or stopping growth; for example, retarding or preventing the growth of a tumor cell.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth. In other examples, suppression of the expression of a protein may include, but not be limited to, reduction in the transcription of a nucleic acid encoding the protein, reduction in the stability of mRNA encoding the protein, inhibition of translation of the protein, reduction in stability of the protein, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth. In other examples, enhancing the expression of a protein may include, but not be limited to, increase in the transcription of a nucleic acid encoding the protein, increase in the stability of mRNA encoding the protein, increase in translation of the protein, increase in the stability of the protein, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth. In other examples, inducing the expression of a protein may include, but not be limited to, increase in the transcription of a nucleic acid encoding the protein, increase in the stability of mRNA encoding the protein, increase in translation of the protein, increase in the stability of the protein, and so forth.

The term "polynucleotide" or "nucleic acid" as used herein refers to a polymeric form of nucleotides of any length, including ribonucleotides and deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. The backbone of the polynucleotide can comprise repeating units, such as N-(2-aminoethyl)-glycine, linked by peptide bonds (i.e., peptide nucleic acid). Alternatively, the backbone of the polynucleotide can comprise a polymer of synthetic subunits such as phosphoramidates and phorphorthioates and thus can be an oligodeoxynucleoside phosphoramidate (P—$NH_2$) or a mixed phosphorothioate-phosphorodiester oligomer or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which modulates and/or engenders an immune response. Generally, the adjuvant is administered in conjunction with an antigen to effect enhancement of an immune response to the antigen as compared to antigen alone. Various adjuvants are described herein.

The terms "CpG oligodeoxynucleotide" and "CpG ODN" herein refer to DNA molecules of 10 to 30 nucleotides in length containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

For any of the structural and functional characteristics described herein, methods of determining these characteristics are known in the art.

As used herein, "microfluidic systems" refers to systems in which low volumes (e.g., mL, nL, pL, fL) of fluids are processed to achieve the discrete treatment of small volumes of liquids. Certain implementations described herein include multiplexing, automation, and high throughput screening. The fluids (e.g., a buffer, a solution, a payload-containing solution, or a cell suspension) can be moved, mixed, separated, or otherwise processed. In certain embodiments described herein, microfluidic systems are used to apply mechanical constriction to a cell suspended in a buffer, inducing perturbations in the cell (e.g., holes) that allow a payload or compound to enter the cytosol of the cell.

As used herein, a "constriction" may refer to a portion of a microfluidic channel defined by an entrance portion, a centerpoint, and an exit portion, wherein the centerpoint is defined by a width, a length, and a depth. In other examples, a constriction may refer to a pore or may be a portion of a pore. The pore may be contained on a surface (e.g., a filter and/or membrane).

For any of the structural and functional characteristics described herein, methods of determining these characteristics are known in the art.

Formulation of PBMCs Comprising Antigens

In some aspects, provided are pharmaceutical formulations comprising PBMCs, the formulation comprising PBMCs wherein the PBMCs comprise at least one antigen, a cryopreservation medium, a hypothermic preservation medium and/or one or more agents that enhance the viability and/or function of PBMCs.

In some embodiments, provided is a pharmaceutical formulation comprising PBMCs, the formulation comprising a) PBMCs wherein the PBMCs comprise at least one antigen, b) a cryopreservation medium, and c) human serum albumin.

In some embodiments, provided is a pharmaceutical formulation comprising PBMCs, the formulation comprising a) PBMCs wherein the PBMCs comprise at least one antigen, b) a cryopreservation medium, c) a hypothermic preservation medium, and d) human serum albumin.

In some embodiments, the formulation comprises about $5 \times 10^4$ to about $5 \times 10^9$ PBMCs. In some embodiments, the formulation comprises about $5 \times 10^6$ to about $5 \times 10^7$ PBMCs. In some embodiments, the formulation comprises about any one of $0.5 \times 10^4$, $1.0 \times 10^4$, $0.5 \times 10^5$, $1.0 \times 10^5$, $0.5 \times 10^6$, $1.0 \times 10^6$, $0.5 \times 10^7$, $1.0 \times 10^7$, $0.5 \times 10^8$, $1.0 \times 10^8$, $0.5 \times 10^9$, $1.0 \times 10^9$ and $5.0 \times 10^9$ PBMCs. In some embodiments, the formulation comprises any one of $0.5 \times 10^4$ to about $1.0 \times 10^4$, about $1.0 \times 10^5$ to about $0.5 \times 10^5$, about $0.5 \times 10^5$ to about $1.0 \times 10^5$, about $1.0 \times 10^5$ to about $0.5 \times 10^6$, about $0.5 \times 10^6$ to about $1.0 \times 10^6$, about $1.0 \times 10^6$ to about $0.5 \times 10^7$, about $0.5 \times 10^7$ to about $1.0 \times 10^7$, about $1.0 \times 10^7$ to about $0.5 \times 10^8$, about $0.5 \times 10^8$ to about $1.0 \times 10^8$, about $1.0 \times 10^8$ to about $0.5 \times 10^9$, about $0.5 \times 10^9$ to about $1.0 \times 10^9$, or about $1.0 \times 10^9$ to about $5 \times 10^9$ PBMCs. In some embodiments, the formulation comprises about any one of $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, and $1 \times 10^8$ PBMCs. In some embodiments, the formulation comprises about $2 \times 10^7$ PBMCs to about $3 \times 10^7$ PBMCs. In some embodiments, the formulation comprises about any one of $2.1 \times 10^7$, $2.2 \times 10^7$, $2.3 \times 10^7$, $2.4 \times 10^7$, $2.5 \times 10^7$, $2.6 \times 10^7$, $2.7 \times 10^7$, $2.8 \times 10^7$, $2.9 \times 10^7$, and $3.0 \times 10^7$ PBMCs. In some embodiments, the formulation comprises about $2.75 \times 10^7$ PBMCs. In some embodiments, the formulation comprises about $2.5 \times 10^7$ PBMCs.

In some embodiments, the volume of the formulation is about 2 mL to about 50 mL. In some embodiments, the volume of the formulation is about 5 mL to about 20 mL. In some embodiments, the volume of the formulation is about any one of 1, 2, 3, 4, 5, 6, 7, 8, 9, 9.5, 10, 10.5, 11, 12, 13, 14, 15, 16, 17, 18, 19, 20, 25, 30, 35, 40, 45, 50 or more mL. In some embodiments, the volume of the formulation is any one of about 1 to about 2, about 2 to about 3, about 3 to about 4, about 4 to about 5, about 5 to about 6, about 6 to about 7, about 7 to about 8, about 8 to about 9, or about 9 to about 10, about 10 to about 11, about 11 to about 12, about 12 to about 13, about 13 to about 14, about 14 to about 15, about 15 to about 16, about 16 to about 17, about 17 to about 18, about 18 to about 19, or about 19 to about 20 mL. In some embodiments, the volume of the formulation is about 10 mL. In some embodiments, the volume of the formulation is about 5 mL.

In some embodiments, the formulation comprises about $1 \times 10^4$ to about $1 \times 10^9$ PBMCs/mL. In some embodiments, the formulation comprises about $1 \times 10^6$ to about $1 \times 10^7$ PBMCs/mL. In some embodiments, the formulation comprises about any one of $1.0 \times 10^4$, $0.5 \times 10^5$, $1.0 \times 10^5$, $0.5 \times 10^6$, $1.0 \times 10^6$, $0.5 \times 10^7$, $1.0 \times 10^7$, $0.5 \times 10^8$, $1.0 \times 10^8$, $0.5 \times 10^9$, and $1.0 \times 10^9$ PBMCs/mL. In some embodiments, the formulation comprises any one of $0.5 \times 10^4$ to about $1.0 \times 10^4$, about $1.0 \times 10^4$ to about $0.5 \times 10^5$, about $0.5 \times 10^5$ to about $1.0 \times 10^5$, about $1.0 \times 10^5$ to about $0.5 \times 10^6$, about $0.5 \times 10^6$ to about $1.0 \times 10^6$, about $1.0 \times 10^6$ to about $0.5 \times 10^7$, about $0.5 \times 10^7$ to about $1.0 \times 10^7$, about $1.0 \times 10^7$ to about $0.5 \times 10^8$, about $0.5 \times 10^8$ to about $1.0 \times 10^8$, about $1.0 \times 10^8$ to about $0.5 \times 10^9$, or about $0.5 \times 10^9$ to about $1.0 \times 10^9$ PBMCs/mL. In some embodiments, the formulation comprises about any one of $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, and $1 \times 10^7$ PBMCs/mL. In some embodiments, the formulation comprises about $2 \times 10^6$ PBMCs/mL to about $3 \times 10^6$ PBMCs/mL. In some embodiments, the formulation comprises about any one of $4 \times 10^6$, $4.2 \times 10^6$, $4.4 \times 10^6$, $4.6 \times 10^6$, $4.8 \times 10^6$, $5.0 \times 10^6$, $5.2 \times 10^6$, $5.4 \times 10^6$, $5.6 \times 10^6$, $5.8 \times 10^6$ and $6 \times 10^6$ PBMCs/mL. In some embodiments, the formulation comprises about $5 \times 10^6$ PBMCs/mL.

In some embodiments, the formulation is sterile. In some embodiments, the formulation comprise less than about 2 EU/mL endotoxin. In some embodiments, the formulation comprise less than any one of about 1, 2, 3, 4, 5, 6, 7, 8, 9, or 10 EU/mL endotoxin. In some embodiments, the formulation is free of mycoplasma.

Formulations of PBMCs Comprising Antigen in Cryopreservation Media

In some embodiments according to any one of the methods described herein, the composition of PBMCs further comprises an agent that enhances the viability and/or function of the PBMCs as compared to a corresponding composition of PBMCs that does not comprise the agent. In some embodiments, the composition of PBMCs further comprises an agent that enhances the viability and/or function of the PBMCs upon freeze-thaw cycle as compared to a corresponding composition of PBMCs that does not comprise the agent. In some embodiments, the agent is a cryopreservation agent and/or a hypothermic preservation agent. In some embodiments, the cryopreservation agent nor the hypothermic preservation agent cause not more than 10% or 20% of cell death in a composition of PBMCs comprising the agent compared to a corresponding composition of PBMCs that does not comprise the agent before any freeze-thaw cycles. In some embodiments, freeze-thaw cycles of PBMC compositions comprising the cryopreservation agent and/or the hypothermic preservation agent causes not more than 10%, 20%, 30%, 40%, or 50% loss in viable cells when compared to a corresponding PBMC composition before the freeze-thaw cycles. In some embodiments, freeze-thaw cycles of PBMC compositions comprising the cryopreservation agent and/or the hypothermic preservation agent causes 10%, 20%, 30%, 40%, or 50% less loss of viable cells when compared to freeze-thaw cycles of a corresponding PBMC without the cryopreservation agent and the hypothermic preservation agent. In some embodiments, at least about 70%, about 80%, about 90%, or about 95% of the PBMCs are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is one or more of mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of Mg2+, Zn2+ or Ca2+. In some embodiments, the agent is one or more of: sodium pyruvate, adenine, trehalose, dextrose, mannose, sucrose, human serum albumin (HSA), dimethyl sulfoxide (DMSO), HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoThermosol®.

In some embodiments according to any one of the methods described herein, the process further comprises a step of incubating the composition of PBMCs with an agent that enhances the viability and/or function of the PBMCs compared to corresponding PBMCs prepared without the further incubation step.

In some embodiments, at least about 50%, about 60%, about 70%, about 80%, about 90%, about 95%, or about 98% of the PBMCs are viable. In some embodiments, at least about 50%, about 60%, about 70%, about 80%, about 90%, about 95%, or about 98% of the PBMCs are viable after storage for at least 3, 6, 9, 12, 15, 18, 24, 30, 36, 42, or 48 months at $\leq-196°$ C. In some embodiments, at least about 50%, about 60%, about 70%, about 80%, about 90%, about 95%, or about 98% of the PBMCs are viable after storage for at least 3, 6, 9, 12, 15, 18, 24, 30, 36, 42, or 48 months at $\leq-120°$ C. In some embodiments, at least about 50%, about 60%, about 70%, about 80%, about 90%, about 95%, or about 98% of the PBMCs are viable after storage for at least 3, 6, 9, 12, 15, 18, 24, 30, 36, 42, or 48 months at $\leq-220°$ C. In some embodiments, at least about 50%, about 60%, about 70%, about 80%, about 90%, about 95%, or about 98% of the PBMCs are viable after up to 1, 2, 3, 4, 5 or more freeze-thaw cycles.

In some embodiments, the formulation comprises about $1 \times 10^4$ to about $1 \times 10^9$ viable PBMCs/mL. In some embodiments, the formulation comprises about $1 \times 10^6$ to about $1 \times 10^7$ viable PBMCs/mL. In some embodiments, the formulation comprises about any one of $1.0 \times 10^4$, $0.5 \times 10^5$, $1.0 \times 10^5$, $0.5 \times 10^6$, $1.0 \times 10^6$, $0.5 \times 10^7$, $1.0 \times 10^7$, $0.5 \times 10^8$, $1.0 \times 10^8$, $0.5 \times 10^9$, and $1.0 \times 10^9$ viable PBMCs/mL. In some embodiments, the formulation comprises any one of $0.5 \times 10^4$ to about $1.0 \times 10^4$, about $1.0 \times 10^4$ to about $0.5 \times 10^5$, about $0.5 \times 10^5$ to about $1.0 \times 10^5$, about $1.0 \times 10^5$ to about $0.5 \times 10^6$, about $0.5 \times 10^6$ to about $1.0 \times 10^6$, about $1.0 \times 10^6$ to about $0.5 \times 10^7$, about $0.5 \times 10^7$ to about $1.0 \times 10^7$, about $1.0 \times 10^7$ to about $0.5 \times 10^8$, about $0.5 \times 10^8$ to about $1.0 \times 10^8$, about $1.0 \times 10^8$ to about $0.5 \times 10^9$, or about $0.5 \times 10^9$ to about $1.0 \times 10^9$ viable PBMCs/mL. In some embodiments, the formulation comprises about any one of $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, and $1 \times 10^7$ viable PBMCs/mL. In some embodiments, the formulation comprises about $2 \times 10^6$ viable PBMCs/mL to about $8 \times 10^6$ viable PBMCs/mL. In some embodiments, the formulation comprises about $3 \times 10^6$ viable PBMCs/mL to about $7 \times 10^6$ viable PBMCs/mL. In some embodiments, the formulation comprises about any one of $3 \times 10^6$, $3.2 \times 10^6$, $3.4 \times 10^6$, $3.6 \times 10^6$, $3.8 \times 10^6$, $4.0 \times 10^6$, $4.2 \times 10^6$, $4.4 \times 10^6$, $4.6 \times 10^6$, $4.8 \times 10^6$ and $5 \times 10^6$ viable PBMCs/mL. In some embodiments, the formulation comprises about $4 \times 10^6$ viable PBMCs/mL.

In some embodiments, the formulation comprises about $1 \times 10^4$ to about $1 \times 10^9$ viable PBMCs/mL after thawing a previously frozen formulation. In some embodiments, the formulation comprises about $1 \times 10^6$ to about $1 \times 10^7$ viable PBMCs/mL post-thaw. In some embodiments, the formulation comprises about any one of $1.0 \times 10^4$, $0.5 \times 10^5$, $1.0 \times 10^5$, $0.5 \times 10^6$, $1.0 \times 10^6$, $0.5 \times 10^7$, $1.0 \times 10^7$, $0.5 \times 10^8$, $1.0 \times 10^8$, $0.5 \times 10^9$, and $1.0 \times 10^9$ viable PBMCs/mL post-thaw. In some embodiments, the formulation comprises any one of $0.5 \times 10^4$ to about $1.0 \times 10^4$, about $1.0 \times 10^4$ to about $0.5 \times 10^5$, about $0.5 \times 10^5$ to about $1.0 \times 10^5$, about $1.0 \times 10^5$ to about $0.5 \times 10^6$, about $0.5 \times 10^6$ to about $1.0 \times 10^6$, about $1.0 \times 10^6$ to about $0.5 \times 10^7$, about $0.5 \times 10^7$ to about $1.0 \times 10^7$, about $1.0 \times 10^7$ to about $0.5 \times 10^8$, about $0.5 \times 10^8$ to about $1.0 \times 10^8$, about $1.0 \times 10^8$ to about $0.5 \times 10^9$, or about $0.5 \times 10^9$ to about $1.0 \times 10^9$ viable PBMCs/mL post-thaw. In some embodiments, the formulation comprises about any one of $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, and $1 \times 10^7$ viable PBMCs/mL post-thaw. In some embodiments, the formulation comprises about $2 \times 10^6$ to about $8 \times 10^6$ viable PBMCs/mL post-thaw. In some embodiments, the formulation comprises about $3\times10^6$ to about $7\times10^6$ viable PBMCs/mL post-thaw. In some embodiments, the formulation comprises about any one of $3\times10^6$, $3.2\times10^6$, $3.4\times10^6$, $3.6\times10^6$, $3.8\times10^6$, $4.0\times10^6$, $4.2\times10^6$, $4.4\times10^6$, $4.6\times10^6$, $4.8\times10^6$ and $5\times10^6$ viable PBMCs/mL post-thaw. In some embodiments, the formulation comprises about $4\times10^6$ viable PBMCs/mL post-thaw.

In some embodiments, the formulation comprises about $5\times10^4$ to about $5\times10^9$ PBMCs. In some embodiments, the formulation comprises about $5\times10^6$ to about $5\times10^7$ PBMCs in about 10 mL. In some embodiments, the formulation comprises about any one of $0.5\times10^4$, $1.0\times10^4$, $0.5\times10^5$, $1.0\times10^5$, $0.5\times10^6$, $1.0\times10^6$, $0.5\times10^7$, $1.0\times10^7$, $0.5\times10^8$, $1.0\times10^8$, $0.5\times10^9$, $1.0\times10^9$ and $5.0\times10^9$ PBMCs in about 5 mL. In some embodiments, the formulation comprises any one of about, about $0.5\times10^4$ to about $1.0\times10^4$, about $1.0\times10^5$ to about $0.5\times10^5$, about $0.5\times10^5$ to about $1.0\times10^5$, about $1.0\times10^5$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, or about $1.0\times10^9$ to about $5\times10^9$ PBMCs in about 10 mL of cryopreservation medium. In some embodiments, the formulation comprises about any one of $0.5\times10^7$, $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ PBMCs in about 5 mL of cryopreservation medium. In some embodiments, the formulation comprises about $2.5\times10^7$ PBMCs in about 5 mL of cryopreservation medium. In some embodiments, the formulation comprises about $2.75\times10^7$ PBMCs in about 5 mL of cryopreservation medium. In some embodiments, the formulation comprises about $2\times10^7$ live PBMCs in about 5 mL of cryopreservation medium. In some embodiments, the formulation comprises about $2.5\times10^7$ PBMCs in about 5 mL of CryoStor® CS10. In some embodiments, the formulation comprises about $2.75\times10^7$ PBMCs in about 5 mL of CryoStor® CS10. In some embodiments, the formulation comprises about $2\times10^7$ live PBMCs in about 5 mL of CryoStor® CS10. In some embodiments, the formulation further comprises about 2% to about 8% (w/w) human serum albumin. In some embodiments, the formulation further comprises about 5% (w/w) human serum albumin.

In some embodiments, the formulation comprises about any one of $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ viable PBMCs in about 5 mL of a solution comprising a cryopreservation medium and a hypothermic preservation medium. In some embodiments, the formulation comprises about $2.0\times10^7$ viable PBMCs in about 5 mL of a solution comprising a cryopreservation medium and a hypothermic preservation medium cryopreservation medium. In some embodiments, the formulation comprises about $2.0\times10^7$ viable PBMCs in about 5 mL of a solution comprising CryoStor® CS10 and HypoThermasol®. In some embodiments, the percentage of CryoStor® CS10 in the formulation is about 50% (w/w) and percentage of HypoThermasol® in the formulation is about 30% (w/w). In some embodiments, the formulation further comprises about 2% to about 8% (w/w) human serum albumin. In some embodiments, the formulation further comprises about 5% (w/w) human serum albumin.

In some embodiments, the formulation comprises about any one of $0.5\times10^4$, $1.0\times10^4$, $0.5\times10^5$, $1.0\times10^5$, $0.5\times10^6$, $1.0\times10^6$, $0.5\times10^7$, $1.0\times10^7$, $0.5\times10^8$, $1.0\times10^8$, $0.5\times10^9$, $1.0\times10^9$ and $5.0\times10^9$ PBMCs in about 5 mL of a solution comprising a cryopreservation medium and a hypothermic preservation medium. In some embodiments, the formulation comprises any one of about, about $0.5\times10^4$ to about $1.0\times10^4$, about $1.0\times10^5$ to about $0.5\times10^5$, about $0.5\times10^5$ to about $1.0\times10^5$, about $1.0\times10^5$ to about $0.5\times10^6$, about $0.5\times10^6$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, or about $1.0\times10^9$ to about $5\times10^9$ PBMCs in about 5 mL of a solution comprising a cryopreservation medium and a hypothermic preservation medium. In some embodiments, the formulation comprises about any one of $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ PBMCs in about 5 mL of a solution comprising a cryopreservation medium and a hypothermic preservation medium. In some embodiments, the formulation comprises about $2.5\times10^7$ PBMCs in about 5 mL of a solution comprising a cryopreservation medium and a hypothermic preservation medium. In some embodiments, the formulation comprises about $2.75\times10^7$ PBMCs in about 5 mL of a solution comprising a cryopreservation medium and a hypothermic preservation medium. In some embodiments, the formulation comprises about $2\times10^7$ live PBMCs in about 5 mL a solution comprising a cryopreservation medium and a hypothermic preservation medium. In some embodiments, the formulation comprises about $2.5\times10^7$ PBMCs in about 5 mL of a solution comprising CryoStor® CS10 and HypoThermasol®. In some embodiments, the formulation comprises about $2.75\times10^7$ PBMCs in about 5 mL of a solution comprising CryoStor® CS10 and HypoThermasol®. In some embodiments, the formulation comprises about $2\times10^7$ live PBMCs in about 5 mL of a solution comprising CryoStor® CS10 and HypoThermasol®. In some embodiments, the percentage of CryoStor® CS10 in the formulation is about 50% (w/w) and percentage of HypoThermasol® in the formulation is about 30% (w/w). In some embodiments, the formulation further comprises about 2% to about 8% (w/w) human serum albumin. In some embodiments, the formulation further comprises about 5% (w/w) human serum albumin.

In some embodiments, the formulation comprises about any one of $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ viable PBMCs in about 5 mL of a solution comprising a cryopreservation medium and a hypothermic preservation medium. In some embodiments, the formulation comprises about $2.0\times10^7$ viable PBMCs in about 5 mL of a solution comprising a cryopreservation medium and a hypothermic preservation medium. In some embodiments, the formulation comprises about viable $2.0\times10^7$ PBMCs in about 5 mL of a solution comprising CryoStor® CS10 and HypoThermasol®. In some embodiments, the percentage of CryoStor® CS10 in the formulation is about 50% (w/w) and percentage of HypoThermasol® in the formulation is about 30% (w/w). In some embodiments, the formulation further comprises about 2% to about 8% (w/w) human serum albumin. In some embodiments, the formulation further comprises about 5% (w/w) human serum albumin. 10082 In some embodiments, the PBMCs in the formulation maintain equal to or greater than about 50% viability up to 1, 2, 3, 4, 5 freeze-thaw cycles. In some embodiments, the PBMCs in the formulation maintain equal to or greater than about 50%, 60%, 70%, 80%, 90%, 95%, or 99% viability up to 1, 2, 3, 4, 5 freeze-thaw cycles. In some embodiments, the PBMCs in the formulation maintain equal to or greater than about 70% viability following storage for at least 12 months at temperatures at or below $-140°$ C. In some embodiments, the PBMCs in the formulation maintain equal to or greater than about 50%, 60%, 70%, 80%, 90%, 95%, or 99% viability following storage for at least 12 months at temperatures at or below −140° C. In some embodiments, the PBMCs in the formulation maintain equal to or greater than about 70% viability following storage for at least 3, 6, 9, 12, 15, 18, 24, 30, or 36 months at temperatures at or below −140° C. In some embodiments, the PBMCs in the formulation maintain equal to or greater than about 70% viability following storage for at least 3 months at temperatures at or below −100° C., −110° C., −120° C., −130° C., −140° C., −150° C., −160° C., −170° C., −180° C., −190° C., or −200° C. In some embodiments, the PBMCs in the formulation maintain equal to or greater than about 70% viability following storage for at least 12 months at temperatures at or below −100° C., −110° C., −120° C., −130° C., −140° C., −150° C., −160° C., −170° C., −180° C., −190° C., or −200° C.

In some embodiments, the pH of the formulation is about 5.0 to about 9.5. In some embodiments, the pH of the formulation is about 6.0 to about 8.5. In some embodiments, the pH of the formulation is about 7.4. In some embodiments, the pH of the formulation is any one of about 5, 5.5, 6, 6.5, 7, 7.5, 8, 8.5, 9 or 10. In some embodiments, the pH of the formulation is any one of about 7, 7.1, 7.2, 7.3, 7.4, 7.5, 7.6, 7.7, 7.8, 7.9, or 8.0. In some embodiments, the pH of the formulation is any one of about 5 to about 6, about 6 to about 7, about 7 to about 8, about 8 to about 9, or about 9 to about 10. In some embodiments, the pH of the formulation is any one of about 7 to about 7.1, about 7.1 to about 7.2, about 7.2 to about 7.3, about 7.3 to about 7.4, about 7.4 to about 7.5, about 7.5 to about 7.6, about 7.6 to about 7.7, about 7.7 to about 7.8, about 7.8 to about 7.9, or about 7.9 to about 8.0.

In some embodiments according to any one of the methods described herein, the process further comprises a step of incubating the composition of PBMCs with an agent that enhances the viability and/or function of the PBMCs compared to corresponding PBMCs prepared without the further incubation step.

In some embodiments, the formulation comprises about any one of $0.5 \times 10^4$, $1.0 \times 10^4$, $0.5 \times 10^5$, $1.0 \times 10^5$, $0.5 \times 10^6$, $1.0 \times 10^6$, $0.5 \times 10^7$, $1.0 \times 10^7$, $0.5 \times 10^8$, $1.0 \times 10^8$, $0.5 \times 10^9$, $1.0 \times 10^9$, $0.5 \times 10^{10}$, $1.0 \times 10^{10}$ PBMCs per mL. In some embodiments, the composition comprises any one of about $0.5 \times 10^4$ to about $1.0 \times 10^4$, about $1.0 \times 10^4$ to about $0.5 \times 10^5$, about $0.5 \times 10^5$ to about $1.0 \times 10^5$, about $1.0 \times 10^5$ to about $0.5 \times 10^6$, about $0.5 \times 10^6$ to about $1.0 \times 10^6$, about $1.0 \times 10^6$ to about $0.5 \times 10^7$, about $0.5 \times 10^7$ to about $1.0 \times 10^7$, about $1.0 \times 10^7$ to about $0.5 \times 10^8$, about $0.5 \times 10^8$ to about $1.0 \times 10^8$, about $1.0 \times 10^8$ to about $0.5 \times 10^9$, or about $0.5 \times 10^9$ to about $1.0 \times 10^9$ PBMCs/mL. In some embodiments, the formulation comprise about any one of $1 \times 10^7$, $1 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $1 \times 10^{11}$ PBMCs/mL. In some embodiments, the formulation comprises about $1 \times 10^6$ PBMCs/mL to about $1 \times 10^7$ PBMCs/mL, wherein PBMCs comprise at least one antigen. In some embodiments, the formulation comprises about $5 \times 10^6$ PBMCs/mL, wherein PBMCs comprise at least one antigen.

In some embodiments, the formulation comprises a cryopreservation medium. In some embodiments, the percentage of the cryopreservation medium in the formulation is any one of 20%, 25%, 30%, 35%, 40%, 45%, 50%, 55%, 60%, 65%, 70%, 75%, 80%, 85%, 90%, 95%, or 98% (w/w). In some embodiments, the percentage of the cryopreservation medium in the formulation is about any one of 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, or 90% to 95% (w/w). In some embodiments, the percentage of the cryopreservation medium in the formulation is about 40% to about 95% (w/w). In some embodiments, the percentage of the cryopreservation medium in the formulation is about 80% (w/w). In some embodiments, the percentage of the cryopreservation medium in the formulation is about 50% (w/w).

In some embodiments, the cryopreservation medium comprises dimethylsulfoxide (DMSO). In some embodiments, the cryopreservation medium comprises about 2% to about 25% DMSO. In some embodiments, the cryopreservation medium comprises about 5% to about 15% DMSO. In some embodiments, the cryopreservation medium comprises about any one of 2%, 3%, 4%, 5%, 6%, 7%, 8%, 9%, 10%, 11%, 12%, 13%, 14%, 15%, 16%, 17%, 18%, 19%, 20%, 21%, 23%, 24%, and 25% DMSO. In some embodiments, the cryopreservation medium comprises any one of about 2% to about 5%, about 5% to about 6%, about 6% to about 7%, about 7% to about 8%, about 8% to about 9%, about 9% to about 10%, about 10% to about 11%, about 11% to about 12%, about 12% to about 13%, about 13% to about 14%, about 14% to about 15%, or about 15% to about 20% DMSO. In some embodiments, the cryopreservation medium comprises about 10% DMSO. In some embodiments, the cryopreservation medium is CryoStor® CS10.

In some embodiments, the formulation comprises a hypothermic preservation medium. In some embodiments, the formulation comprises hypothermic preservation medium at a concentration of about any one of 10%, 15%, 20%, 25%, 30%, 35%, 40%, 45%, 50%, 55%, 60%, 65%, or 70% (w/w). In some embodiments, the percentage of hypothermic preservation medium in the formulation is about any one of 10% to 15%, 15% to 20%, 20% to 25%, 25% to 30%, 30% to 35%, 35% to 40%, 40% to 45%, 45% to 50%, 50% to 55%, 55% to 60%, 60% to 65%, or 65% to 70% (w/w). In some embodiments, the percentage of hypothermic preservation medium in the formulation is about 25% to about 35% (w/w). In some embodiments, the percentage of hypothermic preservation medium in the formulation is about 30%. In some embodiments, the hypothermic preservation medium comprises a water soluble analog of vitamin E. In some embodiments, wherein the hypothermic preservation medium comprises trolox ((±)-6-hydroxy-2,5,7,8-tetramethylchromane-2-carboxylic acid). In some embodiments, the hypothermic preservation medium is HypoThermasol® FRS.

In some embodiments, the human serum albumin is provided in a human serum albumin solution. In some embodiments, the formulation comprises human serum albumin solution at a concentration of about any one of 2%, 3%, 4%, 5%, 8%, 10%, 15%, 20%, 25%, 30%, 35%, 40%, 45%, or 50% (w/w). In some embodiments, the percentage of a human serum albumin solution in the formulation is about any one of 2% to 3%, 3% to 5%, 5% to 8%, 8% to 10%, 10% to 15%, 15% to 20%, 20% to 25%, 25% to 30%, 30% to 35%, 35% to 40%, 40% to 45%, or 45% to 50% (w/w). In some embodiments, the percentage of a human serum albumin solution in the formulation is about 15% to about 25% (w/w). In some embodiments, the percentage of a human serum albumin solution in the formulation is about is about 20% (w/w). In some embodiments, the human albumin solution comprises sodium caprylate at a concentration of about any one of 0.001, 0.01, 0.02, 0.03, 0.04, 0.05, 0.06, 0.07, 0.08, 0.09, 0.1, 0.2, 0.5, or 1 mmol/g of albumin. In some embodiments, the human albumin solution comprises sodium caprylate at a concentration of about 0.08 mmol/g of albumin. In some embodiments, the human albumin solution comprises acetyltryptophan at a concentration of about any one of 0.001, 0.01, 0.02, 0.03, 0.04, 0.05, 0.06, 0.07, 0.08, 0.09, 0.1, 0.2, 0.5, or 1 mmol/g of albumin. In some embodiments, the human albumin solution comprises acetyltryptophan at a concentration of about 0.08 mmol/g of albumin.

In some embodiments, the formulation comprises human serum albumin at a concentration of about any one of 0.5%, 1%, 2%, 3%, 4%, 5%, 6%, 7%, 8%, 9%, 10%, 12%, 15%, 20%, or 25% (w/w). In some embodiments, the percentage of a human serum albumin solution in the formulation is about any one of 0.5% to 1%, 1% to 2%, 2% to 3%, 3% to 4%, 4% to 5%, 5% to 6%, 6% to 7%, 7% to 8%, 8% to 9%, 9% to 10%, 10% to 12%, 12% to 15%, 15% to 20%, or 20% to 25% (w/w). In some embodiments, the percentage of a human serum albumin in the formulation is about is about 2% to about 8% (w/w). In some embodiments, the percentage of a human serum albumin in the formulation is about is about 5% (w/w).

In some embodiments, the pH of the formulation is about 5.0 to about 9.5. In some embodiments, the pH of the formulation is about 6.0 to about 8.5. In some embodiments, the pH of the formulation is any one of about 5, 5.5, 6, 6.5, 7, 7.5, 8, 8.5, 9, 9.5 or 10. In some embodiments, the pH of the formulation is any one of about 7, 7.1, 7.2, 7.3, 7.4, 7.5, 7.6, 7.7, 7.8, 7.9, or 8.0. In some embodiments, the pH of the formulation is any one of about 5 to about 6, about 6 to about 7, about 7 to about 8, about 8 to about 9, or about 9 to about 10. In some embodiments, the pH of the formulation is any one of about 7 to about 7.1, about 7.1 to about 7.2, about 7.2 to about 7.3, about 7.3 to about 7.4, about 7.4 to about 7.5, about 7.5 to about 7.6, about 7.6 to about 7.7, about 7.7 to about 7.8, about 7.8 to about 7.9, or about 7.9 to about 8.0. In some embodiments, the pH of the formulation is about 7.4.

In some embodiments, the cryopreservation medium comprises CryoStor® CS10. In some embodiments, the composition comprising PBMCs comprise about $5 \times 10^6$ to about $5 \times 10^7$ PBMCs in CryoStor® CS10. In some embodiments, the hypothermic preservation medium is HypoThermasol® FRS.

In some embodiments, the formulation is sterile. In some embodiments, the formulation comprise less than about 2 EU/mL endotoxin. In some embodiments, the formulation comprise less than any one of about 1, 2, 3, 4, 5, 6, 7, 8, 9, or 10 EU/mL endotoxin. In some embodiments, the formulation is free of mycoplasma.

In some embodiments, there is provided a pharmaceutical formulation of PBMCs, the formulation comprising: a) about $1 \times 10^6$ PBMCs/mL to about $1 \times 10^7$ PBMCs/mL, wherein PBMCs comprise at least one antigen, b) cryopreservation medium at a percentage of about 65% to about 95% (w/w), and c) human serum albumin about 2% to about 8%, wherein the pH of the formulation is about pH 6.0 to about pH 8.5.

In some embodiments, there is provided a pharmaceutical formulation of PBMCs, the formulation comprising: a) about $5 \times 10^6$ PBMCs/mL, wherein PBMCs comprise at least one antigen, b) cryopreservation medium at a percentage of about 50% (w/w), and c) human serum albumin at a percentage of about 5% (w/w), wherein the pH of the formulation is about pH 7.4.

In some embodiments, there is provided a pharmaceutical formulation of PBMCs, the formulation comprising: a) about $1 \times 10^6$ PBMCs/mL to about $1 \times 10^7$ PBMCs/mL, wherein PBMCs comprise at least one antigen, b) cryopreservation medium at a percentage of about 40% to about 60% (w/w), c) hypothermic preservation medium at a percentage of about 25% to about 35%, and d) human serum albumin about 2% to about 8%, wherein the pH of the formulation is about pH 6.0 to about pH 8.5.

In some embodiments, there is provided a pharmaceutical formulation of PBMCs, the formulation comprising: a) about $5 \times 10^6$ PBMCs/mL, wherein PBMCs comprise at least one antigen, b) cryopreservation medium at a percentage of about 50% (w/w), c) hypothermic preservation medium at a percentage of about 30% (w/w), and d) human serum albumin at a percentage of about 5% (w/w), wherein the pH of the formulation is about pH 7.4.

Vials Comprising Pharmaceutical Formulations

In some embodiments, there is provided a vial comprising any one of the pharmaceutical formulations described herein.

In some aspects, there is provided a vial comprising a pharmaceutical formulation, wherein the pharmaceutical formulation comprises: a) about $5 \times 10^6$ PBMCs to about $5 \times 10^7$ PBMCs, wherein PBMCs comprise at least one antigen, b) cryopreservation medium at a concentration of about 65% to about 95% (w/w), and c) human serum albumin at a concentration about 2% to about 8% (w/w), wherein the pH of the formulation is about pH 6.0 to about pH 8.5. In some embodiments, there is provided a vial comprising a pharmaceutical formulation, wherein the pharmaceutical formulation comprises: a) about $2.5 \times 10^7$ PBMCs, wherein PBMCs comprise at least one antigen, b) cryopreservation medium at a concentration of about 80% (w/w), and c) human serum albumin at a concentration of about 5%, wherein the pH of the formulation is about pH 7.4.

In some aspects, there is provided a vial comprising a pharmaceutical formulation, wherein the pharmaceutical formulation comprises a) about $1 \times 10^6$ PBMCs/mL to about $1 \times 10^7$ PBMCs/mL, wherein PBMCs comprise at least one antigen, b) cryopreservation medium at a concentration of about 40% to about 60% (w/w), c) hypothermic preservation medium about 25% to about 35% (w/w), and d) human serum albumin about 2% to about 8%, wherein the pH of the formulation is about pH 6.0 to about pH 8.5. In some embodiments, there is provided a vial comprising a pharmaceutical formulation, wherein the pharmaceutical formulation comprises: a) about $5 \times 10^6$ PBMCs/mL, wherein PBMCs comprise at least one antigen, b) cryopreservation medium at a concentration of about 50% (w/w), c) hypothermic preservation medium at a concentration of about 30% (w/w), and d) human serum albumin at a concentration of about 5% (w/w), wherein the pH of the formulation is about pH 7.4.

In some embodiments according to any of the vials described herein, the PBMCs are in about 2 mL to about 50 mL of cryopreservation medium. In some embodiments, the PBMCs are in about 5 mL to about 20 mL of cryopreservation medium. In some embodiments, the PBMCs are in about any one of 1, 2, 3, 4, 5, 6, 7, 8, 9, 9.5, 10, 10.5, 11, 12, 13, 14, 15, 16, 17, 18, 19, 20, 25, 30, 35, 40, 45, 50 or more mL of cryopreservation medium. In some embodiments, the PBMCs are in any one of about 1 to about 2, about 2 to about 3, about 3 to about 4, about 4 to about 5, about 5 to about 6, about 6 to about 7, about 7 to about 8, about 8 to about 9, or about 9 to about 10, about 10 to about 11, about 11 to about 12, about 12 to about 13, about 13 to about 14, about 14 to about 15, about 15 to about 16, about 16 to about 17, about 17 to about 18, about 18 to about 19, or about 19 to about 20 mL of cryopreservation medium.

In some embodiments, the cryopreservation medium is CryoStor® CS10. In some embodiments, the cryopreservation medium comprises dimethylsulfoxide (DMSO). In some embodiments, the cryopreservation medium comprises about 2% to about 25% DMSO. In some embodiments, the cryopreservation medium comprises about 5% to about 15% DMSO. In some embodiments, the cryopreservation medium comprises about any one of 2%, 3%, 4%, 5%, 6%, 7%, 8%, 9%, 10%, 11%, 12%, 13%, 14%, 15%, 16%, 17%, 18%, 19%, 20%, 21%, 23%, 24%, and 25% DMSO. In some embodiments, the cryopreservation medium comprises any one of about 2% to about 5%, about 5% to about 6%, about 6% to about 7%, about 7% to about 8%, about 8% to about 9%, about 9% to about 10%, about 10% to about 11%, about 11% to about 12%, about 12% to about 13%, about 13% to about 14%, about 14% to about 15%, or about 15% to about 20% DMSO. In some embodiments, the cryopreservation medium comprises about 10% DMSO.

In some embodiments, the formulation in the vial further comprises about 2% to about 8% (w/w) human serum albumin. In some embodiments, the formulation further comprises about 5% (w/w) human serum albumin.

In some embodiments according to any of the vials described herein, the PBMCs are in about 2 mL to about 50 mL of a solution comprising a cryopreservation medium and a the hypothermic preservation medium. In some embodiments, the PBMCs are in about 5 mL to about 20 mL of a solution comprising a cryopreservation medium and the hypothermic preservation medium. In some embodiments, the PBMCs are in about any one of 1, 2, 3, 4, 5, 6, 7, 8, 9, 9.5, 10, 10.5, 11, 12, 13, 14, 15, 16, 17, 18, 19, 20, 25, 30, 35, 40, 45, 50 or more mL of a solution comprising a cryopreservation medium and a the hypothermic preservation medium. In some embodiments, the PBMCs are in any one of about 1 to about 2, about 2 to about 3, about 3 to about 4, about 4 to about 5, about 5 to about 6, about 6 to about 7, about 7 to about 8, about 8 to about 9, or about 9 to about 10, about 10 to about 11, about 11 to about 12, about 12 to about 13, about 13 to about 14, about 14 to about 15, about 15 to about 16, about 16 to about 17, about 17 to about 18, about 18 to about 19, or about 19 to about 20 mL of a solution comprising a cryopreservation medium and a hypothermic preservation medium. In some embodiments, the solution comprising a cryopreservation medium and a hypothermic preservation medium comprises CryoStor® CS10 and HypoThermasol®. In some embodiments, the percentage of CryoStor® CS10 in the formulation is about 50% (w/w) and percentage of HypoThermasol® in the formulation is about 30% (w/w). In some embodiments, the formulation further comprises about 2% to about 8% (w/w) human serum albumin. In some embodiments, the formulation further comprises about 5% (w/w) human serum albumin.

In some embodiments, the pH of the formulation is about 5.0 to about 9.5. In some embodiments, the pH of the formulation is about 6.0 to about 8.5. In some embodiments, the pH of the formulation is about 7.4. In some embodiments, the pH of the formulation is any one of about 5, 5.5, 6, 6.5, 7, 7.5, 8, 8.5, 9 or 10. In some embodiments, the pH of the formulation is any one of about 7, 7.1, 7.2, 7.3, 7.4, 7.5, 7.6, 7.7, 7.8, 7.9, or 8.0. In some embodiments, the pH of the formulation is any one of about 5 to about 6, about 6 to about 7, about 7 to about 8, about 8 to about 9, or about 9 to about 10. In some embodiments, the pH of the formulation is any one of about 7 to about 7.1, about 7.1 to about 7.2, about 7.2 to about 7.3, about 7.3 to about 7.4, about 7.4 to about 7.5, about 7.5 to about 7.6, about 7.6 to about 7.7, about 7.7 to about 7.8, about 7.8 to about 7.9, or about 7.9 to about 8.0. In some embodiments, the pH of the formulation is about 7.4.

In some embodiments, the formulation in the vial comprises about $5\times10^4$ to about $5\times10^9$ PBMCs. In some embodiments, the formulation comprises about $5\times10^6$ to about $5\times10^7$ PBMCs in about 1 mL to about 10 mL. In some embodiments, the formulation comprises about $5\times10^6$ to about $5\times10^7$ PBMCs in about 1 mL, about 2 mL, about 3 mL, about 4 mL, about 5 mL, about 6 mL, about 7 mL, about 8 mL, about 9 mL, or about 10 mL. In some embodiments, the formulation comprises about any one of $0.5\times10^4$, $1.0\times10^4$, $0.5\times10^5$, $1.0\times10^5$, $0.5\times10^6$, $1.0\times10^6$, $0.5\times10^7$, $1.0\times10^7$, $0.5\times10^8$, $1.0\times10^8$, $0.5\times10^9$, $1.0\times10^9$ and $5.0\times10^9$ PBMCs in about 5 mL. In some embodiments, the formulation comprises any one of about, about $0.5\times10^4$ to about $1.0\times10^4$, about $1.0\times10^5$ to about $0.5\times10^5$, about $0.5\times10^5$ to about $1.0\times10^5$, about $1.0\times10^5$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, or about $1.0\times10^9$ to about $5\times10^9$ PBMCs in about 5 mL of cryopreservation medium. In some embodiments, the formulation comprises about any one of $0.5\times10^7$, $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ PBMCs in about 5 mL of cryopreservation medium. In some embodiments, the formulation comprises about $2.5\times10^7$ PBMCs in about 5 mL of cryopreservation medium. In some embodiments, the formulation further comprises about 2% to about 8% (w/w) human serum albumin. In some embodiments, the formulation further comprises about 5% (w/w) human serum albumin.

In some embodiments, the formulation in the vial comprises any one of about $0.5\times10^4$ to about $1.0\times10^4$, about $1.0\times10^5$ to about $0.5\times10^5$, about $0.5\times10^5$ to about $1.0\times10^5$, about $1.0\times10^5$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, or about $1.0\times10^9$ to about $5\times10^9$ PBMCs in about 5 mL of a solution comprising a cryopreservation medium and a hypothermic preservation medium. In some embodiments, the formulation comprises about any one of $0.5\times10^7$, $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ PBMCs in about 5 mL of mL of a solution comprising a cryopreservation medium and a hypothermic preservation medium. In some embodiments, the formulation comprises about $2.75\times10^7$ PBMCs in about 5 mL of a solution comprising a cryopreservation medium and a hypothermic preservation medium. In some embodiments, the formulation comprises about $2.5\times10^7$ PBMCs in about 5 mL of a solution comprising a cryopreservation medium and a hypothermic preservation medium. In some embodiments, the formulation further comprises about 2% to about 8% (w/w) human serum albumin. In some embodiments, the formulation further comprises about 5% (w/w) human serum albumin.

In some embodiments, the formulation in the vial comprises about $5\times10^4$ to about $5\times10^8$ viable PBMCs. In some embodiments, the formulation comprises about $5\times10^6$ to about $5\times10^7$ viable PBMCs in about 1 mL to about 10 mL. In some embodiments, the formulation comprises about $5\times10^6$ to about $5\times10^7$ viable PBMCs in about 1 mL, about 2 mL, about 3 mL, about 4 mL, about 5 mL, about 6 mL, about 7 mL, about 8 mL, about 9 mL, or about 10 mL volume. In some embodiments, the formulation comprises about any one of $0.5\times10^4$, $1.0\times10^4$, $0.5\times10^5$, $1.0\times10^5$, $0.5\times10^6$, $1.0\times10^6$, $0.5\times10^7$, $1.0\times10^7$, $0.5\times10^8$, $1.0\times10^8$, and $0.5\times10^9$ viable PBMCs in about 5 mL. In some embodiments, the formulation comprises any one of about, about $0.5\times10^4$ to about $1.0\times10^4$, about $1.0\times10^5$ to about $0.5\times10^5$, about $0.5\times10^5$ to about $1.0\times10^5$, about $1.0\times10^5$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, or about $1.0\times10^9$ to about $5\times10^9$ viable PBMCs in about 5 mL of cryopreservation medium. In some embodiments, the formulation comprises about any one of $0.5\times10^7$, $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ viable PBMCs in about 5 mL of cryopreservation medium. In some embodiments, the formulation comprises about $2.75\times10^7$ viable PBMCs in about 5 mL of cryopreservation medium. In some embodiments, the formulation comprises about $2.5\times10^7$ PBMCs in about 5 mL of cryopreservation medium. In some embodiments, the formulation further comprises about 2% to about 8% (w/w) human serum albumin. In some embodiments, the formulation further comprises about 5% (w/w) human serum albumin.

In some embodiments, the formulation in the vial comprises any one of about $0.5\times10^4$ to about $1.0\times10^4$, about $1.0\times10^5$ to about $0.5\times10^5$, about $0.5\times10^5$ to about $1.0\times10^5$, about $1.0\times10^5$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, about $0.5\times10^9$ to about $1.0\times10^9$, or about $1.0\times10^9$ to about $5\times10^9$ viable PBMCs in about 5 mL of a solution comprising a cryopreservation medium and a hypothermic preservation medium. In some embodiments, the formulation comprises about any one of $0.5\times10^7$, $1\times10^7$, $2\times10^7$, $3\times10^7$, $4\times10^7$, $5\times10^7$, $6\times10^7$, $7\times10^7$, $8\times10^7$, $9\times10^7$, and $1\times10^8$ viable PBMCs in about 5 mL of a solution comprising a cryopreservation medium and a hypothermic preservation medium. In some embodiments, the formulation comprises about $2.75\times10^7$ viable PBMCs in about 5 mL of a solution comprising a cryopreservation medium and a hypothermic preservation medium. In some embodiments, the formulation comprises about $2.5\times10^7$ viable PBMCs in about 5 mL of a solution comprising a cryopreservation medium and a hypothermic preservation medium. In some embodiments, the formulation further comprises about 2% to about 8% (w/w) human serum albumin. In some embodiments, the formulation further comprises about 5% (w/w) human serum albumin.

In some embodiments, the formulation in the vial comprises about $1\times10^4$ to about $1\times10^9$ viable PBMCs/mL. In some embodiments, the formulation comprises about $1\times10^6$ to about $1\times10^7$ viable PBMCs/mL. In some embodiments, the formulation comprises about any one of $1.0\times10^4$, $0.5\times10^5$, $1.0\times10^5$, $0.5\times10^6$, $1.0\times10^6$, $0.5\times10^7$, $1.0\times10^7$, $0.5\times10^8$, $1.0\times10^8$, $0.5\times10^9$, and $1.0\times10^9$ viable PBMCs/mL. In some embodiments, the formulation comprises any one of $0.5\times10^4$ to about $1.0\times10^4$, about $1.0\times10^4$ to about $0.5\times10^5$, about $0.5\times10^5$ to about $1.0\times10^5$, about $1.0\times10^5$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, or about $0.5\times10^9$ to about $1.0\times10^9$ viable PBMCs/mL. In some embodiments, the formulation comprises about any one of $1\times10^6$, $2\times10^6$, $3\times10^6$, $4\times10^6$, $5\times10^6$, $6\times10^6$, $7\times10^6$, $8\times10^6$, $9\times10^6$, and $1\times10^7$ viable PBMCs/mL. In some embodiments, the formulation comprises about $2\times10^6$ viable PBMCs/mL to about $8\times10^6$ viable PBMCs/mL. In some embodiments, the formulation comprises about $3\times10^6$ viable PBMCs/mL to about $7\times10^6$ viable PBMCs/mL. In some embodiments, the formulation comprises about any one of $3\times10^6$, $3.2\times10^6$, $3.4\times10^6$, $3.6\times10^6$, $3.8\times10^6$, $4.0\times10^6$, $4.2\times10^6$, $4.4\times10^6$, $4.6\times10^6$, $4.8\times10^6$ and $5\times10^6$ viable PBMCs/mL. In some embodiments, the formulation comprises about $4\times10^6$ viable PBMCs/mL.

In some embodiments, the formulation in the vial comprises about $1\times10^4$ to about $1\times10^9$ viable PBMCs/mL after thawing a previously frozen formulation. In some embodiments, the formulation comprises about $1\times10^6$ to about $1\times10^7$ viable PBMCs/mL post-thaw. In some embodiments, the formulation comprises about any one of $1.0\times10^4$, $0.5\times10^5$, $1.0\times10^5$, $0.5\times10^6$, $1.0\times10^6$, $0.5\times10^7$, $1.0\times10^7$, $0.5\times10^8$, $1.0\times10^8$, $0.5\times10^9$, and $1.0\times10^9$ viable PBMCs/mL post-thaw. In some embodiments, the formulation comprises any one of $0.5\times10^4$ to about $1.0\times10^4$, about $1.0\times10^4$ to about $0.5\times10^5$, about $0.5\times10^5$ to about $1.0\times10^5$, about $1.0\times10^5$ to about $0.5\times10^6$, about $0.5\times10^6$ to about $1.0\times10^6$, about $1.0\times10^6$ to about $0.5\times10^7$, about $0.5\times10^7$ to about $1.0\times10^7$, about $1.0\times10^7$ to about $0.5\times10^8$, about $0.5\times10^8$ to about $1.0\times10^8$, about $1.0\times10^8$ to about $0.5\times10^9$, or about $0.5\times10^9$ to about $1.0\times10^9$ viable PBMCs/mL post-thaw. In some embodiments, the formulation comprises about any one of $1\times10^6$, $2\times10^6$, $3\times10^6$, $4\times10^6$, $5\times10^6$, $6\times10^6$, $7\times10^6$, $8\times10^6$, $9\times10^6$, and $1\times10^7$ viable PBMCs/mL post-thaw. In some embodiments, the formulation comprises about $2\times10^6$ to about $8\times10^6$ viable PBMCs/mL post-thaw. In some embodiments, the formulation comprises about $3\times10^6$ to about $7\times10^6$ viable PBMCs/mL post-thaw. In some embodiments, the formulation comprises about any one of $3\times10^6$, $3.2\times10^6$, $3.4\times10^6$, $3.6\times10^6$, $3.8\times10^6$, $4.0\times10^6$, $4.2\times10^6$, $4.4\times10^6$, $4.6\times10^6$, $4.8\times10^6$ and $5\times10^6$ viable PBMCs/mL post-thaw. In some embodiments, the formulation comprises about $4\times10^6$ viable PBMCs/mL post-thaw.

In some aspects, provided is a pharmaceutical formulation of PBMCs, the formulation comprising about $2.5\times10^7$ PBMCs in about 5 mL of cryopreservation medium, wherein PBMCs comprise at least one antigen, and wherein the pH of the formulation is about pH 7.4. In some aspects, provided is a pharmaceutical formulation of PBMCs, the formulation comprising about $2.75\times10^7$ PBMCs in about 5 mL of cryopreservation medium, wherein PBMCs comprise at least one antigen, and wherein the pH of the formulation is about pH 7.4. In some embodiments, the cryopreservation medium is CryoStor® CS10.

In some aspects, provided is a pharmaceutical formulation of PBMCs, the formulation comprising about $2.5\times10^7$ PBMCs in about 5 mL of a solution comprising a cryopreservation medium and a hypothermic preservation medium, wherein PBMCs comprise at least one antigen, and wherein the pH of the formulation is about pH 7.4. In some aspects, provided is a pharmaceutical formulation of PBMCs, the formulation comprising about $2.75\times10^7$ PBMCs in about 5 mL of a solution comprising a cryopreservation medium and a hypothermic preservation medium, wherein PBMCs comprise at least one antigen, and wherein the pH of the formulation is about pH 7.4. In some embodiments, the cryopreservation medium is CryoStor® CS10. In some embodiments, the hypothermic preservation medium is HypoThermasol®. In some embodiments, the percentage of CryoStor® CS10 in the formulation is about 50% (w/w) and percentage of HypoThermasol® in the formulation is about 30% (w/w). In some embodiments, the formulation further comprises about 2% to about 8% (w/w)

human serum albumin. In some embodiments, the formulation further comprises about 5% (w/w) human serum albumin.

Compositions of PBMCs Comprising HPV Antigens

In some embodiments, the PBMCs comprise an HPV antigen and an adjuvant delivered intracellularly. In some embodiments, the PBMCs comprising the at least one HPV antigen are conditioned. In some embodiments, the PBMCs comprising the at least one HPV antigen are conditioned by a process comprising incubating the PBMCs with an adjuvant for about 2 hours to about 10 hours, about 3 hours to about 6 hours, or about 4 hours at about 37° C. for the PBMCs to condition.

In some embodiments, the method comprises administering an effective amount of PBMCs comprising at least one HPV antigen, wherein the PBMCs comprising the at least one HPV antigen are prepared by: a) passing a cell suspension comprising input PBMCs through a cell-deforming constriction, wherein a diameter of the constriction is a function of a diameter of the input PBMCs in the suspension, thereby causing perturbations of the input PBMCs large enough for the at least one HPV antigen to pass through to form perturbed input PBMCs; and b) incubating the perturbed input PBMCs with the at least one HPV antigen for a sufficient time to allow the at least one HPV antigen to enter the perturbed input PBMCs; thereby generating modified PBMCs comprising the at least one HPV antigen. In some embodiments, the HPV antigen comprises the amino acid sequence of any one of SEQ ID NOs:1-3 and 18-25. In some embodiments, the HPV antigen comprises an amino acid sequence with at least 90% identity to any one of SEQ ID NOs:1-3 and 18-25.

In some embodiments, the method comprises administering an effective amount of PBMCs comprising an HPV antigen and an adjuvant, wherein the PBMCs comprising the HPV antigen and the adjuvant are prepared by: a) passing a cell suspension comprising input PBMCs through a cell-deforming constriction, wherein a diameter of the constriction is a function of a diameter of the input PBMCs in the suspension, thereby causing perturbations of the input PBMCs large enough for the HPV antigen and the adjuvant to pass through to form perturbed input PBMCs; and b) incubating the perturbed input PBMCs with the HPV antigen and the adjuvant for a sufficient time to allow the HPV antigen and the adjuvant to enter the perturbed input PBMCs; thereby generating modified PBMCs comprising the HPV antigen and the adjuvant. In some embodiments, the HPV antigen comprises the amino acid sequence of any one of SEQ ID NOs: 1-3 and 18-255. In some embodiments, the HPV antigen comprises an amino acid sequence with at least 90% identity to any one of SEQ ID NOs: 1-3 and 18-25.

In some aspects, there is provided a composition of PBMCs comprising at least one HPV antigen, wherein the PBMCs comprising the at least one HPV antigen are prepared by: a) passing a cell suspension comprising input PBMCs through a cell-deforming constriction, wherein a diameter of the constriction is a function of a diameter of the input PBMCs in the suspension, thereby causing perturbations of the input PBMCs large enough for the at least one HPV antigen to pass through to form perturbed input PBMCs; and b) incubating the perturbed input PBMCs with the at least one HPV antigen for a sufficient time to allow the at least one HPV antigen to enter the perturbed input PBMCs; thereby generating modified PBMCs comprising the at least one HPV antigen. In some embodiments, the HPV antigen comprises the amino acid sequence of any one of SEQ ID NOs: 1-3 and 18-25. In some embodiments, the HPV antigen comprises an amino acid sequence with at least 90% identity to any one of SEQ ID NOs: 1-3 and 18-25.

In some embodiments, the width of the constriction is about 10% to about 99% of the mean diameter of the input PBMCs. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input PBMCs having the smallest diameter within the population of PBMCs. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input PBMCs. In some embodiments, the width of the constriction about 3 μm to about 5 μm, about 3 μm to about 3.5 μm, about 3.5 μm to about 4 μm, about 4 μm to about 4.5 μm, about 3.2 μm to about 3.8 μm, about 3.8 μm to about 4.3 μm, about 4.2 μm to about 6 μm, or about 4.2 μm to about 4.8 μm. In some embodiments, the width of the constriction is about 4.5 μm. In some embodiments, the width of the constriction is about or less than any one of 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the cell suspension comprising the input PBMCs are passed through multiple constrictions wherein the multiple constrictions are arranged in series and/or in parallel. In some embodiments, the cell suspension comprising the input PBMCs are passed through multiple constrictions wherein the multiple constrictions are arranged in series and/or in parallel.

In some embodiments, the HPV antigen is a pool of multiple polypeptides that elicit a response against the same and or different HPV antigens. In some embodiments, the HPV antigen is a polypeptide comprising one or more antigenic HPV epitope and one or more heterologous peptide sequences. In some embodiments, the HPV antigen complexes with other antigens or with an adjuvant. In some embodiments, the HPV antigen is capable of being processed into an MHC class I-restricted peptide. In some embodiments, the HPV antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), R837, R848, a TLR3 agonist, a TLR4 agonist or a TLR9 agonist. In some embodiments, the adjuvant is polyinosinic-polycytidylic acid (poly I:C).

Methods of Generating Compositions of PBMCs Comprising an Antigen

In some embodiments, provided are methods for generating a composition comprising PBMCs comprising at least one antigen, wherein the at least one antigen is delivered to the PBMCs intracellularly. In some embodiments, provided are methods for generating a composition comprising PBMCs comprising a antigen and an adjuvant, wherein the antigen and the adjuvant is delivered to the PBMCs intracellularly.

In some embodiments, the PBMCs comprising the at least one antigen are prepared by a process comprising: a) passing a cell suspension comprising a population of input PBMCs through a cell-deforming constriction, wherein a diameter of the constriction is a function of a diameter of the input PBMCs in the suspension, thereby causing perturbations of the input PBMCs large enough for the at least one antigen to pass through to form perturbed input PBMCs; and b) incubating the population of perturbed input PBMCs with the at least one antigen and the adjuvant for a sufficient time to allow the antigen to enter the perturbed input PBMCs, thereby generating the modified PBMCs comprising the at least one antigen.

In some embodiments, the antigen is a HPV antigen. In some embodiments, the HPV antigen comprises a peptide derived from HPV E6. In some embodiments, the HPV antigen comprises a peptide derived from HPV E7. In some embodiments, the HPV antigen comprises a peptide derived from HPV E6

In some embodiments, the width of the constriction is about 10% to about 99% of the mean diameter of the input PBMCs. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input PBMCs. In some embodiments, the width of the constriction is about 3 μm to about 15 μm. In some embodiments, the width of the constriction is about 3 μm to about 10 μm. In some embodiments, the width of the constriction is about 3 μm to about 6 μm. In some embodiments, the width of the constriction is about 4.2 μm to about 6 μm. In some embodiments, the width of the constriction is about 4.2 μm to about 4.8 μm. In some embodiments, the width of the constriction is about 3 μm to about 5 μm. In some embodiments, the width of the constriction is about 3 μm to about 3.5 μm. In some embodiments, the width of the constriction is about 3.5 μm to about 4 μm. In some embodiments, the width of the constriction is about 4 μm to about 4.5 μm. In some embodiments, the width of the constriction is about 3.2 μm to about 3.8 μm. In some embodiments, the width of the constriction is about 3.8 μm to about 4.3 μm. In some embodiments, the width of the constriction is about or less than any one of 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the width of the constriction is about or less than any one of 3.0 μm, 3.1 μm, 3.2 μm, 3.3 μm, 3.4 μm, 3.5 μm, 3.6 μm, 3.7 μm, 3.8 μm, 3.9 μm, 4.0 μm, 4.1 μm, 4.2 μm, 4.3 μm, 4.4 μm, 4.5 μm, 4.6 μm, 4.7 μm, 4.8 μm, 4.9 μm, or 5.0 μm. In some embodiments, the width of the constriction is about 4.5 μm. In some embodiments, the cell suspension comprising the input PBMCs are passed through multiple constrictions wherein the multiple constrictions are arranged in series and/or in parallel.

In some embodiments, the HPV antigen is a pool of multiple polypeptides that elicit a response against the same and or different HPV antigens. In some embodiments, the HPV antigen is a polypeptide comprising one or more antigenic HPV epitope and one or more heterologous peptide sequences. In some embodiments, the HPV antigen is delivered with other antigens or with an adjuvant. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV is HPV-16 or HPV-18. In some embodiments, the HPV antigen is comprised of an HLA-A2-specific epitope. In some embodiments, the HPV antigen is an HPV E6 antigen or an HPV E7 antigen. In some embodiments, the antigen comprises a peptide derived from HPV E6 and/or E7. In some embodiments, the antigen comprises an HLA-A2-restricted peptide derived from HPV E6 and/or E7. In some embodiments, the HPV antigen is capable of being processed into an MHC class I-restricted peptide. In some embodiments, the HPV antigen is capable of being processed into an MHC class II-restricted peptide.

In some embodiments, the composition further comprises an adjuvant. In some embodiments, the adjuvant is a CpG oligodeoxynucleotide (ODN), LPS, IFN-α, IFN-β, IFN-γ, alpha-Galactosyl Ceramide, STING agonists, cyclic dinucleotides (CDN), RIG-I agonists, polyinosinic-polycytidylic acid (poly I:C), R837, R848, a TLR3 agonist, a TLR4 agonist or a TLR9 agonist. In some embodiments, the adjuvant is polyinosinic-polycytidylic acid (poly I:C).

In some aspects, provided is a method of producing any one of the formulations of PBMCs described herein. In some aspects, provided is a method of producing a formulation of PBMCs, the method comprising adding a cryopreservation medium and human serum albumin to a population of PBMCs wherein the PBMCs comprise at least one antigen.

In some embodiments according to the methods described herein for producing a formulation of PBCs, a) the population of PBMCs in the formulation is about $1\times10^4$ PBMCs/mL to about $1\times10^{10}$ PBMCs/mL, b) the cryopreservation medium is added to a percentage of about 20% to about 98% (w/w), and c) the human serum albumin is added to a concentration of about 0.5% to about 25% (w/w), wherein the pH of the formulation is adjusted to about pH 5.0 to about pH 9.5. In some embodiments, a) the population of PBMCs in the formulation is about $1\times10^6$ PBMCs/mL to about $1\times10^7$ PBMCs/mL, b) the cryopreservation medium is added to a percentage of about 65% to about 95% (w/w), and c) the human serum albumin is added to a concentration of about 2% to about 8% (w/w), wherein the pH of the formulation is adjusted to about pH 6.0 to about pH 8.5. In some embodiments, a) the population of PBMCs in the formulation is about $6\times10^6$ PBMCs, b) the cryopreservation medium is added to a percentage of about 80% (w/w), and c) the human serum albumin is added to a percentage of about 5% (w/w), wherein the pH of the formulation is adjusted to about pH 7.4.

In some embodiments according to the methods described herein for producing a formulation of PBCs, a) the population of PBMCs in the formulation is about $1\times10^4$ PBMCs to about $1\times10^{10}$ PBMCs, b) the cryopreservation medium is added to a percentage of about 20% to about 80% (w/w), c) the hypothermic preservation medium is added to a percentage of about 15% to about 45% (w/w), and d) the human serum albumin solution is added to a percentage of about 5% to about 35% (w/w), wherein the pH of the formulation is adjusted to about pH 5.0 to about pH 9.5. In some embodiments, a) the population of PBMCs in the formulation is about $1\times10^6$ PBMCs to about $1\times10^7$ PBMCs, b) the cryopreservation medium is added to a percentage of about 40% to about 60% (w/w), c) the hypothermic preservation medium is added to a percentage of about 25% to about 35% (w/w), and d) the human serum albumin solution is added to a percentage of about 15% to about 25% (w/w), wherein the pH of the formulation is adjusted to about pH 6.0 to about pH 8.5. In some embodiments, a) the population of PBMCs in the formulation is about $6 \times 10^6$ PBMCs, b) the cryopreservation medium is added to a percentage of about 50% (w/w), c) the hypothermic preservation medium is added to a percentage of about 30% (w/w), and d) the human serum albumin solution is added to a percentage of about 20% (w/w), wherein the pH of the formulation is adjusted to about pH 7.4. In some embodiments, the percentage of human serum albumin in the formulation (added via the human serum albumin solution) is about 2% to about 8% (w/w). In some embodiments, the percentage of human serum albumin in the formulation is about 5% (w/w).

In some embodiments, the formulation comprises about any one of $1.0 \times 10^4$, $0.5 \times 10^5$, $1.0 \times 10^5$, $0.5 \times 10^6$, $1.0 \times 10^6$, $0.5 \times 10^7$, $1.0 \times 10^7$, $0.5 \times 10^8$, $1.0 \times 10^8$, $0.5 \times 10^9$, $1.0 \times 10^9$, $0.5 \times 10^{10}$, $1.0 \times 10^{10}$ PBMCs per mL. In some embodiments, the composition comprises any one of about $0.5 \times 10^4$ to about $1.0 \times 10^4$, about $1.0 \times 10^5$ to about $0.5 \times 10^5$, about $0.5 \times 10^5$ to about $1.0 \times 10^5$, about $1.0 \times 10^5$ to about $0.5 \times 10^6$, about $0.5 \times 10^6$ to about $1.0 \times 10^6$, about $1.0 \times 10^6$ to about $0.5 \times 10^7$, about $0.5 \times 10^7$ to about $1.0 \times 10^7$, about $1.0 \times 10^7$ to about $0.5 \times 10^8$, about $0.5 \times 10^8$ to about $1.0 \times 10^8$, about $1.0 \times 10^8$ to about $0.5 \times 10^9$, or about $0.5 \times 10^9$ to about $1.0 \times 10^9$ PBMCs/mL. In some embodiments, the formulation comprise about any one of $1 \times 10^7$, $1 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $1 \times 10^{11}$ PBMCs/mL. In some embodiments, the formulation comprises about $1 \times 10^6$ PBMCs/mL to about $1 \times 10^7$ PBMCs/mL, wherein the PBMCs comprise at least one antigen. In some embodiments, the formulation comprises about $6 \times 10^6$ PBMCs/mL, wherein the PBMCs comprise at least one antigen. In some embodiments, the formulation comprises about $5 \times 10^6$ PBMCs/mL, wherein the PBMCs comprise at least one antigen. In some embodiments, the formulation comprises about $4 \times 10^6$ PBMCs/mL, wherein PBMCs comprise at least one antigen.

In some embodiments, the method comprises adding a cryopreservation medium to a predetermined percentage. In some embodiments, the cryopreservation medium is added to a percentage of about any one of 20%, 25%, 30%, 35%, 40%, 45%, 50%, 55%, 60%, 65%, 70%, 75%, 80%, 85%, 90%, 95%, or 98% (w/w). In some embodiments, the cryopreservation medium is added to a percentage of about any one of 20% to 25%, 25% to 30%, 30% to 35%, 35% to 40%, 40% to 45%, 45% to 50%, 50% to 55%, 55% to 60%, 60% to 65%, 65% to 70%, 70% to 75%, 75% to 80%, 80% to 85%, 85% to 90%, or 90% to 95% (w/w). In some embodiments, the cryopreservation medium is added to a percentage of about 80% (w/w). In some embodiments, the cryopreservation medium is added to a percentage of about 50% (w/w). In some embodiments, the cryopreservation medium is CryoStor® CS10.

CryoStor® CS10 (BioLife Solution) is a serum-free, protein-free, defined cryopreservation medium containing 10% DMSO that is used as a cryoprotectant, an osmolality agent, and for pH control. CryoStor® CS10 is pre-formulated with DMSO, a cryoprotective agent which helps mitigate cell damage from the formation of intracellular ice In some embodiments, the cryopreservation medium comprises dimethylsulfoxide (DMSO). In some embodiments, the cryopreservation medium comprises about 2% to about 25% DMSO. In some embodiments, the cryopreservation medium comprises about 5% to about 15% DMSO. In some embodiments, the cryopreservation medium comprises about any one of 2%, 3%, 4%, 5%, 6%, 7%, 8%, 9%, 10%, 11%, 12%, 13%, 14%, 15%, 16%, 17%, 18%, 19%, 20%, 21%, 23%, 24%, and 25% DMSO. In some embodiments, the cryopreservation medium comprises any one of about 2% to about 5%, about 5% to about 6%, about 6% to about 7%, about 7% to about 8%, about 8% to about 9%, about 9% to about 10%, about 10% to about 11%, about 11% to about 12%, about 12% to about 13%, about 13% to about 14%, about 14% to about 15%, or about 15% to about 20% DMSO. In some embodiments, the cryopreservation medium comprises about 10% DMSO.

In some embodiments, the method comprises adding a hypothermic preservation medium to a predetermined percentage. In some embodiments, the hypothermic preservation medium is added to a percentage of about any one of 10%, 15%, 20%, 25%, 30%, 35%, 40%, 45%, 50%, 55%, 60%, 65%, or 70% (w/w). In some embodiments, the hypothermic preservation medium is added to a percentage of about any one of 10% to 15%, 15% to 20%, 20% to 25%, 25% to 30%, 30% to 35%, 35% to 40%, 40% to 45%, 45% to 50%, 50% to 55%, 55% to 60%, 60% to 65%, or 65% to 70% (w/w). In some embodiments, the hypothermic preservation medium is added to a percentage of about 25% to about 35% (w/w). In some embodiments, the hypothermic preservation medium is added to a percentage of about 30%. In some embodiments, the hypothermic preservation medium comprises a water soluble analog of vitamin E. In some embodiments, wherein the hypothermic preservation medium comprises trolox ((±)-6-hydroxy-2,5,7,8-tetramethylchromane-2-carboxylic acid). In some embodiments, the hypothermic preservation medium is HypoThermasol® FRS.

HypoThermosol® FRS (BioLife Solution) is a serum-free, protein-free, DMSO-free hypothermic preservation medium that is similar in composition to CryoStor® CS10. The difference is that CryoStor® CS10 contains DMSO which is replaced with Trolox (a water-soluble analog of Vitamin E) for HypoThermosol® FRS.

In some embodiments, the method comprises adding human serum albumin to a predetermined percentage. In some embodiments, the human serum albumin is added to a percentage of about any one of 0.5%, 1%, 2%, 3%, 4%, 5%, 6%, 7%, 8%, 9%, 10%, 12%, 15%, 20%, or 25% (w/w). In some embodiments, the human serum albumin is added to a percentage of about any one of 0.5% to 1%, 1% to 2%, 2% to 3%, 3% to 4%, 4% to 5%, 5% to 6%, 6% to 7%, 7% to 8%, 8% to 9%, 9% to 10%, 10% to 12%, 12% to 15%, 15% to 20%, or 20% to 25% (w/w). In some embodiments, the human serum albumin is added to a percentage of about 2% to about 8% (w/w). In some embodiments, the human serum albumin is added to a percentage of about 5% (w/w). In some embodiments, the human serum albumin is added to a percentage of about 15% to about 25% (w/w). In some embodiments, the human serum albumin is added to a percentage of about 20% (w/w).

In some embodiments, the formulation is produced by adding an albumin solution to the formulation. In some embodiments, the albumin solution is added to a final percentage of about 15% to about 35%. In some embodiments, the albumin solution is added to a final percentage of about 15%, about 20%, about 25%, about 30%, or about 35%. In some embodiments, the albumin solution is an Albumin (Human), USP, 25% Solution. Albumin (Human), USP, 25% Solution is a sterile preparation of albumin for intravenous administration. Albumin (Human) is a 25% sterile solution of albumin in an aqueous diluent. The preparation is stabilized with sodium caprylate (about 0.08 mmol/g albumin) and acetyltryptophan (about 0.08 mmol/g albumin). It is a clear, slightly viscous liquid, which can range from almost colorless, to yellow, amber or green. In some embodiment, the albumin solution contains no preservative.

In some embodiments, the pH of the formulation is about 5.0 to about 9.5. In some embodiments, the pH of the formulation is about 6.0 to about 8.5. In some embodiments, the pH of the formulation is about 7.4. In some embodiments, the pH of the formulation is any one of about 5, 5.5, 6, 6.5, 7, 7.5, 8, 8.5, 9 or 10. In some embodiments, the pH of the formulation is any one of about 7, 7.1, 7.2, 7.3, 7.4, 7.5, 7.6, 7.7, 7.8, 7.9, or 8.0. In some embodiments, the pH of the formulation is any one of about 5 to about 6, about 6 to about 7, about 7 to about 8, about 8 to about 9, or about 9 to about 10. In some embodiments, the pH of the formulation is any one of about 7 to about 7.1, about 7.1 to about 7.2, about 7.2 to about 7.3, about 7.3 to about 7.4, about 7.4 to about 7.5, about 7.5 to about 7.6, about 7.6 to about 7.7, about 7.7 to about 7.8, about 7.8 to about 7.9, or about 7.9 to about 8.0.

Antigens

In some embodiments according to the methods described herein, the exogenous antigen is a HPV antigen. Papillomaviruses are small nonenveloped DNA viruses with a virion size of ~55 nm in diameter. More than 100 HPV genotypes are completely characterized, and a higher number is presumed to exist. HPV is a known cause of cervical cancers, as well as some vulvar, vaginal, penile, oropharyngeal, anal, and rectal cancers. Although most HPV infections are asymptomatic and clear spontaneously, persistent infections with one of the oncogenic HPV types can progress to precancer or cancer. Other HPV-associated diseases can include common warts, plantar warts, flat warts, anogenital warts, anal lesions, epidermodysplasia, focal epithelial hyperplasia, mouth papillomas, verrucous cysts, laryngeal papillomatosis, squamous intraepithelial lesions (SILs), cervical intraepithelial neoplasia (CIN), vulvar intraepithelial neoplasia (VIN) and vaginal intraepithelial neoplasia (VAIN). Many of the known HPV types cause benign lesions with a subset being oncogenic. Based on epidemiologic and phylogenetic relationships, HPV types are classified into fifteen "high-risk types" (HPV 16, 18, 31, 33, 35, 39, 45, 51, 52, 56, 58, 59, 68, 73, and 82) and three "probable high-risk types" (HPV 26, 53, and 66), which together are known to manifest as low and high grade cervical changes and cancers, as well as other anogential cancers such as vulval, vaginal, penile, anal, and perianal cancer, as well as head and neck cancers. Recently, the association of high-risk types HPV 16 and 18 with breast cancer was also described. Eleven HPV types classified as "low-risk types" (HPV 6, 11, 40, 42, 43, 44, 54, 61, 70, 72, and 81) are known to manifest as benign low-grade cervical changes, genital warts and recurrent respiratory papillomatosis. Cutaneous HPV types 5, 8, and 92 are associated with skin cancer. In some HPV-associated cancers, the immune system is depressed and correspondingly, the antitumor response is significantly impaired. See Suresh and Burtness, *Am J Hematol Oncol* 13(6):20-27 (2017). In some embodiments, the exogenous antigen is a pool of multiple polypeptides that elicit a response against the same and or different antigens. In some embodiments, an antigen in the pool of multiple antigens does not decrease the immune response directed toward other antigens in the pool of multiple antigens. In some embodiments, the HPV antigen is a polypeptide comprising an antigenic HPV epitope and one or more heterologous peptide sequences. In some embodiments, the HPV antigen complexes with itself, with other antigens, or with the adjuvant. In some embodiments, the HPV is HPV-16 or HPV-18. In some embodiments, the HPV antigen is comprised of an HLA-A2-specific epitope. In some embodiments, the HPV antigen is an HPV E6 antigen or an HPV E7 antigen. In some embodiments, the antigen comprises a peptide derived from HPV E6 and/or E7. In some embodiments, the antigen comprises an HLA-A2-restricted peptide derived from HPV E6 and/or E7. In some embodiments, the HLA-A2-restricted peptide comprises the amino acid sequence of any one of SEQ ID NOs: 1-4. In some embodiments, the HLA-A2-restricted peptide comprises the amino acid sequence of any one of SEQ ID NOs:18-25. In some embodiments, the HPV antigen comprises an amino acid sequence with at least 90% similarity to any one of SEQ ID NOs:18-25. In some embodiments, the HPV antigen comprises an amino acid sequence with at least 90% similarity to SEQ ID NO:1. In some embodiments, the HPV antigen comprises an amino acid sequence with at least 90% similarity to SEQ ID NO:2. In some embodiments, the HPV antigen comprises the amino acid sequence of SEQ ID NO:3. In some embodiments, the HPV antigen comprises an amino acid sequence with at least 90% similarity to SEQ ID NO:4. In a some embodiment, the HPV antigen consists of the amino acid sequence of SEQ ID NO:18. In some embodiments, the HPV antigen comprises the amino acid sequence of SEQ ID NO:19. In a some embodiments, the HPV antigen consists of the amino acid sequence of SEQ ID NO:20. In a some embodiments, the HPV antigen consists of the amino acid sequence of SEQ ID NO:21. In a some embodiments, the HPV antigen consists of the amino acid sequence of SEQ ID NO:22. In a some embodiments, the HPV antigen consists of the amino acid sequence of SEQ ID NO:23. In a some embodiments, the HPV antigen consists of the amino acid sequence of SEQ ID NO:24. In a some embodiments, the HPV antigen consists of the amino acid sequence of SEQ ID NO:25. In some embodiments, the HPV antigen comprises the amino acid sequence of any one of SEQ ID NOs:18-25. In some embodiments, the HPV antigen is a plurality of antigens comprising at least one of the amino acid sequences of any one of SEQ ID NOs:18-25. In some embodiments, the exogenous antigen is a plurality of antigens comprising 2, 3, 4, 5, 6, 7 or 8 of the amino acid sequences of any one of SEQ ID Nos:18-25. In some embodiments, the exogenous antigen is a plurality of antigens comprising an amino acid sequence with at least 90% similarity to SEQ ID NO:19 and an amino acid sequence with at least 90% similarity to SEQ ID NO:23. In some embodiments, the exogenous antigen is a plurality of antigens comprising the amino acid sequence of SEQ ID NO:19 and the amino acid sequence of SEQ ID NO:23. In some embodiments, the plurality of antigens is contained within a pool of non-covalently linked peptides. In some embodiments, the plurality of antigens is contained within a pool of non-covalently linked peptides, wherein each peptide comprises no more than one antigen. In some embodiments, the plurality of antigens is contained within a pool of non-covalently linked peptides, wherein the amino acid sequence of SEQ ID NO:19 and the amino acid sequence of SEQ ID NO:23 are contained within separate peptides.

In some embodiments, the HPV antigen is within a pool of multiple polypeptides that elicit a response against the same and or different HPV antigens. In some embodiments, an antigen in the pool of multiple antigens does not decrease the immune response directed toward other antigens in the pool of multiple antigens. In some embodiments, the HPV antigen is a polypeptide comprising an antigenic HPV antigen and one or more heterologous peptide sequences. In some embodiments, the HPV antigen complexes with itself, with other antigens, or with the adjuvant. In some embodiments, the HPV antigen is comprised of an HLA-A2-specific epitope. In some embodiments, the HPV antigen is comprised of an HLA-A11-specific epitope. In some embodiments, HPV antigen is comprised of an HLA-B7-specific epitope. In some embodiments, the HPV antigen is comprised of an HLA-C8-specific epitope. In some embodiments, the HPV antigen comprises part or all of the N-terminal domain of a full-length HPV protein.

In some embodiments according to any one of the methods described herein, the PBMCs comprise a plurality of HPV antigens that comprise a plurality of immunogenic epitopes. In further embodiments, following administration to an individual of the PBMCs comprising the plurality of antigens that comprise the plurality of immunogenic epitopes, none of the plurality of immunogenic epitopes decreases an immune response in the individual to any of the other immunogenic epitopes. In some embodiments, the HPV antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the HPV antigen is a polypeptide comprising an immunogenic peptide epitope and one or more heterologous peptide sequences. In some embodiments, the HPV antigen is a polypeptide comprising an immunogenic peptide epitope that is flanked on the N-terminus and/or the C-terminus by heterologous peptide sequences. In some embodiments, the flanking heterologous peptide sequences are derived from disease-associated immunogenic peptides. In some embodiments, the flanking heterologous peptide sequences are non-naturally occurring sequence. In some embodiments, the flanking heterologous peptide sequences are derived from an immunogenic synthetic long peptide (SLP). In some embodiments, the HPV antigen is capable of being processed into an MHC class I-restricted peptide and/or an MHC class II-restricted peptide.

Adjuvants

As used herein, the term "adjuvant" can refer to a substance which either directly or indirectly modulates and/or engenders an immune response. In some embodiments of the invention, an adjuvant is delivered intracellularly to a population of PBMCs to form modified PBMCs comprising the adjuvant. In some instances, the adjuvant is administered in conjunction with PBMCs comprising a HPV antigen to effect enhancement of an immune response to the HPV antigen as compared to HPV antigen alone. In some embodiments, the PBMCs are incubated with the adjuvant before, during, or after the passage of PBMCs through the constrictions, to facilitate conditioning (for example but not limited to maturation) of the PBMCs. Adjuvants can be used to boost elicitation of an immune cell response (e.g. T cell response) to a HPV antigen. Exemplary adjuvants include, without limitation, stimulator of interferon genes (STING) agonists, retinoic acid-inducible gene I (RIG-I) agonists, and agonists for TLR3, TLR4, TLR7, TLR8 and/or TLR9. Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is CpG ODN, LPS, IFN-α, IFN-β, IFN-γ, alpha-Galactosyl Ceramide, STING agonists, cyclic dinucleotides (CDN), RIG-I agonists, polyinosinic:polycytidylic acid (polyI:C), R837, R848, a TLR3 agonist, a TLR4 agonist or a TLR9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT (SEQ ID NO:30)) or CpG ODN 2006 (also known as CpG 7909) (TCGTCGTTTTGTCGTTTTGTCGTT (SEQ ID NO:31)) oligonucleotide. In some embodiments, the adjuvant is CpG 7909. In some embodiments, the RIG-I agonist comprises polyinosinic:polycytidylic acid (polyI:C). Multiple adjuvants can also be used in conjunction with HPV antigens to enhance the elicitation of immune response. In some embodiments, the PBMCs comprising the HPV antigen further comprise more than one adjuvant. In some embodiments, the PBMCs comprising the HPV antigen is conditioned by more than one adjuvant. Multiple adjuvants can also be used in conjunction with HPV antigens to enhance the elicitation of immune response. In some embodiments, the PBMCs comprising the HPV antigen further comprise more than one adjuvant. In some embodiments, the PBMCs comprising the HPV antigen further comprise any combination of the adjuvants CpG ODN, LPS, IFN-α, IFN-β, IFN-γ, alpha-Galactosyl Ceramide, STING agonists, cyclic dinucleotides (CDN), RIG-I agonists, polyinosinic:polycytidylic acid (polyI:C), R837, R848, a TLR3 agonist, a TLR4 agonist or a TLR9 agonist. In some embodiments, the PBMCs comprising the HPV antigen are conditioned by any combination of the adjuvants CpG ODN, LPS, IFN-α, IFN-β, IFN-γ, alpha-Galactosyl Ceramide, STING agonists, cyclic dinucleotides (CDN), RIG-I agonists, polyinosinic:polycytidylic acid (polyI:C), R837, R848, a TLR3 agonist, a TLR4 agonist or a TLR9 agonist.

Constituent Cells within the PBMCs

In some embodiments, the methods disclosed herein provide for the administration to an individual in need thereof an effective amount of compositions of PBMCs comprising at least one antigen, wherein the at least one antigen is delivered intracellularly. In some embodiments, the methods disclosed herein provide for the administration to an individual in need thereof an effective amount of compositions of PBMCs comprising at least one HPV antigen, wherein the at least one HPV antigen is delivered intracellularly. In some embodiments, the composition of PBMCs comprises a plurality of PBMCs. In some embodiments, the PBMCs are one or more of T cells, B cells, NK cells, monocytes, dendritic cells and/or NK-T cells.

In a particular embodiment of the invention, the cells comprising a HPV antigen of the composition are PBMCs. As used herein, PBMCs may be isolated by apheresis such as leukapheresis from whole blood obtained from an individual. Also provided are PBMC compositions reconstituted by mixing different pools of PBMCs from the same individual or different individuals. In other examples, PBMCs may also be reconstituted by mixing different populations of cells into a mixed cell composition with a generated profile. In some embodiments, the populations of cells used for reconstituting PBMCs are mixed populations of cells (such as a mixture of one or more of T cells, B cells, NK cells or monocytes). In some embodiments, the populations of cells used for reconstituting PBMCs are purified populations of cells (such as purified T cells, B cells, NK cells or monocytes). In additional examples, the different populations of cells used in reconstituting a PBMC composition can be isolated from the same individual (e.g. autologous) or isolated from different individuals (e.g. allogenic and/or heterologous).

Therefore, in some embodiments according to the methods described herein, the plurality of PBMCs comprises one or more of T cells, B cells, NK cells, monocytes, dendritic cells or NK-T cells. In some embodiments, the plurality of PBMCs comprises T cells, B cells, NK cells, monocytes, dendritic cells or NK-T cells. In some embodiments, the plurality of PBMCs comprises one or more of CD3+ T cells, CD20+ B cells, CD14+ monocytes, CD56+ NK cells. In some embodiments, the plurality of PBMCs comprises T cells, B cells, NK cells and monocytes, and the ratio of T cells, B cells, NK cells and monocytes to the total number of PBMCs in the plurality of PBMCs is essentially the same as the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs is essentially the same as the ratio of T cells, B cells, NK cells and monocytes to the total number of PBMCs in a leukapheresis product from whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 1%, 2%, 5%, 10% 15%, 20%, 25%, 30%, 40%, or 50% from the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 10% from the ratio of T cells, B cells, NK cells and monocytes to the total number of PBMCs in whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 1%, 2%, 5%, 10% 15%, 20%, 25%, 30%, 40%, or 50% from the ratio of T cells, B cells, NK cells and monocytes to the total number of PBMCs in a leukapheresis product from whole blood. In some embodiments, the plurality of PBMCs comprises T cells, B cells, NK cells and monocytes, and the ratio of T cells, B cells, NK cells and monocytes to the total number of PBMCs in the plurality of PBMCs differs by not more than any one of 10% from the ratio of T cells, B cells, NK cells and monocytes to the total number of PBMCs in a leukapheresis product from whole blood.

In some embodiments according to the methods described herein, about 25% to about 70% of the modified PBMCs are T cells. In some embodiments, about 2.5% to about 14% of the modified PBMCs are B cells. In some embodiments, about 3.5% to about 35% of the modified PBMCs are NK cells. In some embodiments, about 4% to about 25% of the modified PBMCs are NK cells.

In some embodiments according to the methods described herein, at least about any one of 15%, 20%, 25%, 30%, 35%, 40%, 45%, 50%, 55%, 60%, 65%, 70%, 75%, or 80% of the PBMCs are T cells. In some embodiments, at least about 25% of the PBMCs are T cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the PBMCs are B cells. In some embodiments, at least about 1.5% of the PBMCs are B cells. In some embodiments, at least about any one of 0.5%, 1%, 1.5%, 2%, 2.5%, 3%, 4%, 5%, 6%, 7%, 7.5%, 8%, 9%, 10%, 11%, 12%, 13%, 14%, 15%, 16%, 17%, 18%, 19%, 20%, 25%, or 30% of the PBMCs are NK cells. In some embodiments, at least about 3% of the PBMCs are NK cells. In some embodiments, at least about any one of 1%, 2%, 3%, 4%, 5%, 6%, 7%, 8%, 9%, 10%, 12%, 14%, 16%, 18%, 20%, 25%, 30%, 35% or 40% of the PBMCs are monocytes. In some embodiments, at least about 4% of the PBMCs are monocytes. In some embodiments, at least about 25% of the PBMCs are T cells; at least about 1.5% of the PBMCs are B cells; at least about 3% of the PBMCs are NK cells; and at least about 4% of the PBMCs are monocytes.

In some embodiments according to the methods described herein, not more than about any one of 40%, 45%, 50%, 55%, 60%, 65%, 70%, 75%, 80%, 85%, or 90% of the PBMCs are T cells. In some embodiments, not more than about 70% of the PBMCs are T cells. In some embodiments, not more than about any one of 5%, 10%, 12%, 14%, 16%, 18%, 20%, 22%, 25%, 30%, 35%, 40%, or 50% of the PBMCs are B cells. In some embodiments, not more than about 30% of the PBMCs are B cells. In some embodiments, not more than about any one of 10%, 15%, 20%, 25%, 30%, 35%, 40%, 45%, 50% or 60% of the PBMCs are NK cells. In some embodiments, not more than about 20% of the PBMCs are NK cells. In some embodiments, not more than about any one of 5%, 10%, 12%, 14%, 16%, 18%, 20%, 22%, 25%, 30%, 35%, 40%, or 50% of the PBMCs are monocytes. In some embodiments, not more than about 45% of the PBMCs are monocytes. In some embodiments, not more than about 80% of the PBMCs are T cells; not more than about 30% of the PBMCs are B cells; not more than about 20% of the PBMCs are NK cells; and not more than about 45% of the PBMCs are monocytes.

In some embodiments according to the methods described herein, about any one of 20% to 25%, 25% to 30%, 30% to 35%, 35% to 40%, 40% to 45%, 45% to 50%, 50% to 55%, 55% to 60%, 60% to 65%, 65% to 70%, 70% to 75%, or 75% to 80% of the modified PBMCs are T cells. In some embodiments, about 25% to about 80% of the modified PBMCs are T cells. In some embodiments, about any one of 1% to 1.5%, 1.5% to 2.5%, 2.5% to 4%, 4% to 6%, 6% to 8%, 8% to 10%, 10% to 12%, 12% to 14%, 14% to 16%, 16% to 20%, 20% to 25%, or 25% to 30% of the modified PBMCs are B cells. In some embodiments, about 1.5% to about 30% of the modified PBMCs are B cells. In some embodiments, about any one of 1% to 2%, 2% to 3%, 3% to 5%, 5% to 8%, 8% to 10%, 10% to 12%, 12% to 14%, 14% to 16%, 16% to 20%, 20% to 25%, 25% to 30%, 30% to 35%, or 35% to 40% of the modified PBMCs are NK cells. In some embodiments, about 3.0% to about 35% of the modified PBMCs are NK cells. In some embodiments, about any one of 2% to 4%, 4% to 6%, 6% to 8%, 8% to 10%, 10% to 12%, 12% to 14%, 14% to 16%, 16% to 20%, 20% to 25%, 25% to 30%, 30% to 35%, 35% to 40%, or 30% to 45% of the modified PBMCs are monocytes. In some embodiments, about 4% to about 45% of the modified PBMCs are monocytes. In some embodiments, about 25% to about 80% of the modified PBMCs are T cells, about 1.5% to about 30% of the modified PBMCs are B cells, about 3% to about 35% of the modified PBMCs are NK cells, and about 4% to about 45% of the modified PBMCs are monocytes. In some embodiments, about 25% to about 80% of the modified PBMCs are T cells, about 1.5% to about 30% of the modified PBMCs are B cells, about 3% to about 20% of the modified PBMCs are NK cells, and about 4% to about 45% of the modified PBMCs are monocytes. In some embodiments, about 25% to about 80% of the modified PBMCs are T cells, about 1.5% to about 30% of the modified PBMCs are B cells, about 3.0% to about 20% of the modified PBMCs are NK cells, and about 4% to about 45% of the modified PBMCs are monocytes.

As used herein, PBMCs can also be generated after manipulating the composition of a mixed cell population of mononuclear blood cells (such as lymphocytes and monocytes). In some instances, the PBMCs are generated after reducing (such as depleting) certain subpopulations (such as B cells) within a mixed cell population of mononuclear blood cells. The composition in a mixed cell population of mononuclear blood cells in an individual can be manipulated to make the cell population more closely resemble a leukapheresis product from whole blood in the same individual. In other examples, the composition in a mixed cell population of mononuclear blood cells (for example, mouse splenocytes) can also be manipulated to make the cell population more closely resemble human PBMCs isolated from a leukapheresis product from human whole blood.

In some embodiments of the invention, the composition of PBMCs comprising at least one HPV antigen is a population of cells found in PBMCs. In some embodiments, the composition of PBMCs comprising at least one HPV antigen comprises one or more of T cells, B cells, NK cells, monocytes, dendritic cells or NK-T cells. In some embodiments, the composition of PBMCs comprising at least one HPV antigen comprises one or more of CD3+ T cells, CD20+ B cells, CD14+ monocytes, CD56+ NK cells. In some embodiments, the composition of PBMCs comprising at least one HPV antigen comprises at least about any of 70%, 75%, 80%, 85%, 90%, 95%, or 99% T cells. In some embodiments, the composition of PBMCs comprising at least one HPV antigen comprises 100% T cells. In some embodiments, the composition of PBMCs comprising at least one HPV antigen antigen comprises at least about any of 70%, 75%, 80%, 85%, 90%, 95%, or 99% B cells. In some embodiments, the composition of PBMCs comprising at least one HPV antigen comprises 100% B cells. In some embodiments, the composition of PBMCs comprising at least one HPV antigen comprises at least about any of 70%, 75%, 80%, 85%, 90%, 95%, or 99% NK cells. In some embodiments, the composition of PBMCs comprising at least one HPV antigen comprises 100% NK cells. In some embodiments, the composition of PBMCs comprising at least one HPV antigen comprises at least about any of 70%, 75%, 80%, 85%, 90%, 95%, or 99% monocytes. In some embodiments, the composition of PBMCs comprising at least one HPV antigen comprises 100% monocytes. In some embodiments, the composition of PBMCs comprising at least one HPV antigen comprises at least about any of 70%, 75%, 80%, 85%, 90%, 95%, or 99% dendritic cells. In some embodiments, the composition of PBMCs comprising at least one HPV antigen comprises 100% dendritic cells. In some embodiments, the composition of PBMCs comprising at least one HPV antigen comprises at least about any of 70%, 75%, 80%, 85%, 90%, 95%, or 99% NK-T cells. In some embodiments, the composition of PBMCs comprising at least one HPV antigen comprises 100% NK-T cells.

Constrictions Used in Generating Compositions of PBMCs Comprising HPV Antigen

In some embodiments, the invention provides compositions of PBMCs comprising a HPV antigen for stimulating an immune response. In some embodiments, the HPV antigen is delivered to the PBMCs intracellularly. Methods of introducing payloads to PBMCs are known in the art.

In some embodiments, the HPV antigen is introduced into the PBMCs by passing the cell through a constriction such that transient pores are introduced to the membrane of the cell thereby allowing the HPV antigen to enter the cell. Examples of constriction-based delivery of compounds into a cell are provided by WO 2013/059343, WO 2015/023982, WO 2016/070136, WO2017041050, WO2017008063, WO 2017/192785, WO 2017/192786, WO 2019/178005, WO 2019/178006, WO 2020/072833, WO 2020/154696, and WO 2020/176789.

In some embodiments, the HPV antigen and adjuvant are delivered into the PBMCs to produce the PBMCs of the invention by passing a cell suspension comprising the PBMCs through a constriction, wherein the constriction deforms the input PBMCs thereby causing a perturbation of the input PBMCs such that a HPV antigen and an adjuvant enter the perturbed input PBMCs. In some embodiments, the constriction is contained within a microfluidic channel. In some embodiments, multiple constrictions can be placed in parallel and/or in series within the microfluidic channel.

In some embodiments, the constriction within the microfluidic channel includes an entrance portion, a center point, and an exit portion. In some embodiments, the length, depth, and width of the constriction within the microfluidic channel can vary. In some embodiments, the width of the constriction within the microfluidic channel is a function of the diameter of the PBMCs cells. Methods to determine the diameter of PBMCs are known in the art; for example, high-content imaging, cell counters or flow cytometry.

In some embodiments, the width of the constriction is about 10% to about 99% of the mean diameter of the input PBMCs. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input PBMCs having the smallest diameter within the population of PBMCs. In some embodiments, the width of the constriction is any one of about 10% to about 90%, about 10% to about 80%, about 10% to about 70%, about 20% to about 60%, about 40% to about 60%, about 30% to about 45%, about 50% to about 99%, about 50% to about 90%, about 50% to about 80%, about 50% to about 70%, about 60% to about 90%, about 60% to about 80%, or about 60% to about 70% of the mean diameter of the input PBMCs.

In some embodiments of the constriction-based delivery of an HPV antigen to PBMCs, the width of the constriction is about 3 μm to about 15 μm. In some embodiments, the width of the constriction is about 3 μm to about 10 μm. In some embodiments, the width of the constriction is about 3 μm to about 6 μm. In some embodiments, the width of the constriction is about 4.2 μm to about 6 μm. In some embodiments, the width of the constriction is about 4.2 μm to about 4.8 μm. In some embodiments, the width of the constriction is about 3 μm to about 5 μm. In some embodiments, the width of the constriction is about 3 μm to about 3.5 μm. In some embodiments, the width of the constriction is about 3.5 μm to about 4 μm. In some embodiments, the width of the constriction is about 4 μm to about 4.5 μm. In some embodiments, the width of the constriction is about 3.2 µm to about 3.8 µm. In some embodiments, the width of the constriction is about 3.8 µm to about 4.3 µm. In some embodiments, the width of the constriction is about or less than any one of 2 µm, 2.5 µm, 3 µm, 3.5 µm, 4 µm, 4.5 µm, 5 µm, 5.5 µm, 6 µm, 6.5 µm, 7 µm, 7.5 µm, 8 µm, 8.5 µm, 9 µm, 9.5 µm, 10 µm, 10.5 µm, 11 µm, 11.5 µm, 12 µm, 12.5 µm, 13 µm, 13.5 µm, 14 µm, 14.5 µm or 15 µm. In some embodiments, the width of the constriction is about or less than any one of 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, or 5.0 µm. In some embodiments, the width of the constriction is about 4.5 µm.

Examples of parameters that may influence the delivery of the compound into the PBMCs include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the cell concentration, the concentration of the compound in the cell suspension, buffer in the cell suspension, and the amount of time that PBMCs recover or incubate after passing through the constrictions can affect the passage of the delivered compound into the PBMCs. Additional parameters influencing the delivery of the compound into the PBMCs can include the velocity of the input PBMCs in the constriction, the shear rate in the constriction, the viscosity of the cell suspension, the velocity component that is perpendicular to flow velocity, and time in the constriction. In addition, multiple chips comprising channels in series and/or in parallel may impact delivery to PBMCs. Multiple chips in parallel may be useful to enhance throughput. Such parameters can be designed to control delivery of the compound. In some embodiments, the cell concentration ranges from about 10 to at least about $10^{12}$ cells/mL or any concentration or range of concentrations therebetween. In some embodiments, delivery compound concentrations can range from about 10 ng/mL to about 1 g/mL or any concentration or range of concentrations therebetween. In some embodiments, delivery compound concentrations can range from about 1 pM to at least about 2 M or any concentration or range of concentrations therebetween.

In some embodiments, the concentration of HPV antigen incubated with the PBMCs is between about 0.01 µM and about 10 mM. For example, in some embodiments, the concentration of HPV antigen incubated with the PBMCs is any of less than about 0.01 µM, about 0.1 µM, about 1 µM, about 10 µM, about 100 µM, about 1 mM or about 10 mM. In some embodiments, the concentration of HPV antigen incubated with the PBMCs is greater than about 10 mM. In some embodiments, the concentration of HPV antigen incubated with the PBMCs is any of between about 0.01 µM and about 0.1 µM, between about 0.1 µM and about 1 µM, between about 1 µM and about 10 µM, between about 10 µM and about 100 µM, between about 100 µM and about 1 mM, or between 1 mM and about 10 mM. In some embodiments, the concentration of HPV antigen incubated with the PBMCs is between about 0.1 µM and about 1 mM. In some embodiments, the concentration of HPV antigen incubated with the PBMCs is between about 0.1 µM and about 10 µM. In some embodiments, the concentration of HPV antigen incubated with the PBMCs is 1 µM.

In some embodiments, the molar ratio of antigen to adjuvant incubated with the perturbed input PBMCs is any of between about 10000:1 to about 1:10000. For example, in some embodiments, the molar ratio of antigen to adjuvant incubated with the perturbed input PBMCs is about any of 10000:1, about 1000:1, about 100:1, about 10:1, about 1:1, about 1:10, about 1:100, about 1:1000, or about 1:10000. In some embodiments, the molar ratio of antigen to adjuvant incubated with the perturbed input P is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the molar ratio of antigen to adjuvant incubated with the perturbed input PBMCs is about 200:1. In some embodiments, the molar ratio of antigen to adjuvant incubated with the perturbed input PBMCs is about 20:1.

In some embodiments, the modified PBMCs comprise the adjuvant at a concentration between about 1 nM and about 1 mM. For example, in some embodiments, the modified PBMCs comprise the adjuvant at a concentration of any of less than about 0.01 µM, about 0.1 µM, about 1 µM, about 10 µM, about 100 µM, about 1 mM or about 10 mM. In some embodiments, the modified PBMCs comprise the adjuvant at a concentration of greater than about any of 10 mM. in some embodiments, the modified PBMCs comprise the adjuvant at a concentration of any of between about 1 nM to about 10 nM, about 0.1 µM and about 1 µM, between about 1 µM and about 10 µM, between about 10 µM and about 100 µM, between about 100 µM and about 1 mM, or between 1 mM and about 10 mM. In some embodiments, the modified PBMCs comprise the adjuvant at a concentration between about 0.1 µM and about 1 mM. In some embodiments, the modified PBMCs comprise the adjuvant at a concentration of about 1 µM.

In some embodiments, the modified PBMCs comprise the antigen at a concentration between about 1 nM and about 1 mM. For example, in some embodiments, the modified PBMCs comprises the antigen at a concentration of any of less than about 0.01 µM, about 0.1 µM, about 1 µM, about 10 µM, about 100 µM, about 1 mM or about 10 mM. In some embodiments, the modified PBMCs comprise the antigen at a concentration of greater than about any of 10 mM. in some embodiments, the modified PBMCs comprise the antigen at a concentration of any of between about 1 nM to about 10 nM, about 0.1 µM and about 1 µM, between about 1 µM and about 10 µM, between about 10 µM and about 100 µM, between about 100 µM and about 1 mM, or between 1 mM and about 10 mM. In some embodiments, the modified PBMCs comprise the antigen at a concentration between about 0.1 µM and about 1 mM. In some embodiments, the modified PBMCs comprise the antigen at a concentration of about 1 µM.

In some embodiments, the molar ratio of antigen to adjuvant in the modified PBMCs is any of between about 10000:1 to about 1:10000. For example, in some embodiments, the molar ratio of antigen to adjuvant in the modified PBMCs is about any of 10000:1, about 1000:1, about 100:1, about 10:1, about 1:1, about 1:10, about 1:100, about 1:1000, or about 1:10000. In some embodiments, the molar ratio of antigen to adjuvant in the modified PBMCs is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the molar ratio of antigen to adjuvant in the modified PBMCs is about 200:1. In some embodiments, the molar ratio of antigen to adjuvant in the modified PBMCs is about 20:1.

Conditioning of PBMCs

In some embodiments according to any one of methods described herein, the PBMCs comprising at least one antigen are conditioned. In some embodiments according to any one of methods described herein, the PBMCs comprising at least one HPV antigen are conditioned. In further embodiments, the PBMCs are matured. In some embodiments, the PBMCs are conditioned subsequent to constriction mediated delivery. In some embodiments, the PBMCs comprising the at least one HPV antigen are incubated with an adjuvant for a sufficient time for the cells comprising the constriction-delivered HPV antigens to condition, thereby generating a composition of conditioned cells comprising the at least one HPV antigen. In some embodiments, the PBMCs are conditioned subsequent to constriction-mediated delivery. In some embodiments, the PBMCs comprising the constriction-delivered HPV antigens are incubated with an adjuvant for a sufficient time for the PBMCs comprising the constriction-delivered mutated HPV antigens to condition, thereby generating a composition of conditioned PBMCs comprising the at least one HPV antigen. In some embodiments, the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist. In some embodiments, the adjuvant is CpG ODN 2006 (also known as CpG 7909) (TCGTCGTTTTGTCGTTTTGTCGTT (SEQ ID NO:31)). In some embodiments, the adjuvant is CpG 7909. In some embodiments, the adjuvant is a CpG 7909 oligodeoxynucleotide (ODN).

In some aspects, there is provided a composition of conditioned PBMCs comprising at least one HPV antigen, prepared by a process comprising the steps of: a) passing a cell suspension comprising a population of input PBMCs through a cell-deforming constriction, wherein a width of the constriction is a function of the input PBMCs in the suspension, thereby causing perturbations of the input PBMCs large enough for the at least one HPV antigen to pass through to form perturbed input PBMCs; b) incubating the perturbed input PBMCs with the at least one HPV antigen for a sufficient time to allow the at least one HPV antigen to enter the perturbed PBMCs, thereby generating modified PBMCs comprising the at least one HPV antigen; and c) incubating the modified PBMCs comprising the constriction-delivered HPV antigens with an adjuvant for a sufficient time for the modified PBMCs comprising the constriction-delivered HPV antigens to condition, thereby generating the composition of conditioned PBMCs comprising the at least one HPV antigen. In some embodiments, the process further comprises isolating the modified PBMCs comprising the HPV antigen from the cell suspension before incubation with the adjuvant to condition the modified PBMCs. In some embodiments, the adjuvant is a CpG 7909 oligodeoxynucleotide (ODN).

In some embodiments, the PBMCs are conditioned prior to constriction-mediated delivery. In some embodiments, the PBMCs are incubated with an adjuvant for a sufficient time for the PBMCs to condition, thereby conditioning the PBMCs. In some embodiments, there is provided a composition of conditioned PBMCs comprising at least one HPV antigen, prepared by a process comprising the steps of: a) incubating PBMCs with an adjuvant for a sufficient time for the PBMCs to condition, thereby generating conditioned PBMCs; b) passing a cell suspension comprising the conditioned PBMCs through a cell-deforming constriction, wherein a width of the constriction is a function of a diameter of the PBMCs in the suspension, thereby causing perturbations of the PBMCs large enough for the at least one HPV antigen to pass through to form conditioned perturbed PBMCs; and c) incubating the conditioned perturbed PBMCs with the at least one HPV antigen for a sufficient time to allow the at least one HPV antigen to enter the conditioned perturbed PBMCs, thereby generating the conditioned PBMCs comprising the at least one HPV antigen. In some embodiments, the process further comprises isolating the conditioned PBMCs from the adjuvant before passing the conditioned PBMCs through a cell-deforming constriction. In some embodiments, the adjuvant is a CpG 7909 oligodeoxynucleotide (ODN).

In some embodiments according to any one of methods described herein, the PBMCs comprising the at least one HPV antigen are incubated with the adjuvant for about 1 to about 24 hours for the PBMCs to condition. In some embodiments, the PBMCs are incubated with the adjuvant for about 2 to about 10 hours for the PBMCs to condition. In some embodiments, the PBMCs are incubated with the adjuvant for about 3 to about 6 hours for the PBMCs to condition. In some embodiments, the PBMCs are incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the PBMCs to condition. In some embodiments, the PBMCs are incubated with the adjuvant for about 4 hours for the PBMCs to condition. In some embodiments, the PBMCs are incubated with the adjuvant at about 37° C. for about 4 hours for the PBMCs to condition. In some embodiments, the PBMCs are incubated with CpG 7909 for about 4 hours for the PBMCs to condition. In some embodiments, the PBMCs are incubated with the CpG 7909 at about 37° C. for about 4 hours for the PBMCs to condition. In some embodiments, the PBMCs are incubated with the CpG 7909 at a concentration of about any of 0.20 mg/mL, 0.25 mg/mL, 0.30 mg/mL, 0.35 mg/mL, 0.40 mg/mL, 0.45 mg/mL, or 0.50 mg/mL, or any concentration therebetween. In some embodiments, the PBMCs are incubated with the CpG 7909 at a concentration of about 0.35 mg/mL. In some embodiments, the PBMCs are incubated with the CpG 7909 at a concentration of about 0.35 mg/mL and at about 37° C. for about 4 hours for the PBMCs to condition.

In some embodiments, there is provided a conditioned plurality of PBMCs comprising at least one HPV antigen, prepared by incubating the plurality of PBMCs comprising the at least one HPV antigen with an adjuvant for a sufficient time for the PBMCs to condition, thereby generating the conditioned plurality of PBMCs comprising the at least one HPV antigen. In some embodiments, there is provided a conditioned plurality of PBMCs comprising at least one HPV antigen, prepared by incubating the plurality of PBMCs with an adjuvant for a sufficient time for the PBMCs to condition prior to introducing the at least one HPV antigen to the PBMCs, thereby generating the conditioned plurality of PBMCs comprising the at least one HPV antigen.

In some embodiments according to any of the conditioned plurality of PBMCs described herein, the plurality of PBMCs is incubated with the adjuvant for about 1 to about 24 hours for the PBMCs to condition. In some embodiments, the plurality of PBMCs is incubated with the adjuvant for about 2 to about 10 hours for the PBMCs to condition. In some embodiments, the plurality of PBMCs is incubated with the adjuvant for about 3 to about 6 hours for the PBMCs to condition. In some embodiments, the plurality of PBMCs is incubated with the adjuvant for any one of about 1 hour, 2 hours, 3 hours, 3.5 hours, 4 hours, 4.5 hours, 5 hours, 5.5 hours, 6 hours, 8 hours, 12 hours, 16 hours, 20 hours, or 24 hours for the PBMCs to condition. In some embodiments, the plurality of PBMCs is incubated with the adjuvant for about 4 hours for the PBMCs to condition. In some embodiments, the PBMCs are incubated with the adjuvant at a temperature of about any one of: 4, 8, 12, 16, 20, 25, 26, 27, 28, 29, 30, 31, 32, 33, 34, 35, 36, 37, 38, 39 or 40° C. In some embodiments, the PBMCs are incubated with the adjuvant at about 37° C. In some embodiments, the PBMCs comprising the at least one HPV antigen are conditioned by a process comprising incubating the PBMCs with an adjuvant for about 2 hours to about 10 hours, about 3 hours to about 6 hours, or about 4 hours at about 37° C. for the PBMCs to condition. In some embodiments, the PBMCs are incubated with CpG 7909 for about 4 hours for the PBMCs to condition. In some embodiments, the PBMCs are incubated with the CpG 7909 at about 37° C. for about 4 hours for the PBMCs to condition. In some embodiments, the PBMCs are incubated with the CpG 7909 at a concentration of about any of 0.20 mg/mL, 0.25 mg/mL, 0.30 mg/mL, 0.35 mg/mL, 0.40 mg/mL, 0.45 mg/mL, or 0.50 mg/mL, or any concentration therebetween. In some embodiments, the PBMCs are incubated with the CpG 7909 at a concentration of about 0.35 mg/mL. In some embodiments, the PBMCs are incubated with the CpG 7909 at a concentration of about 0.35 mg/mL and at about 37° C. for about 4 hours for the PBMCs to condition.

In some embodiments according to any one of the conditioned plurality of PBMCs described herein, one or more co-stimulatory molecules are upregulated in the conditioned plurality of modified PBMCs compared to an unconditioned plurality of modified PBMCs. In some embodiments, one or more co-stimulatory molecules are upregulated in a subpopulation of cells in the conditioned plurality of modified PBMCs compared to the subpopulation of cells in an unconditioned plurality of modified PBMCs. In some embodiments, one or more co-stimulatory molecules are upregulated in the B cells of the conditioned plurality of modified PBMCs compared to the B cells in an unconditioned plurality of modified PBMCs. In some embodiments, the co-stimulatory molecule is CD80 and/or CD86. In some embodiments, the co-stimulatory molecule is CD86. In some embodiments, the CD80 and/or CD86 is upregulated in the B cells of the conditioned plurality of modified PBMCs by more than about 1.2-fold, 1.5-fold, 1.8-fold, 2-fold, 3-fold, 4-fold, 5-fold, 8-fold, or more than 10-fold compared to the B cells in an unconditioned plurality of modified PBMCs. In some embodiments, the CD80 and/or CD86 is upregulated in the B cells of the conditioned plurality of modified PBMCs by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold compared to the B cells in an unconditioned plurality of modified PBMCs. In some embodiments, the expression of one or more of IFN-γ, IL-6, MCP-1, MIP-1β, IP-10, or TNF-α is increased in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased a subpopulation of cells in the conditioned plurality compared to the subpopulation of cells in an unconditioned plurality of modified PBMCs. In some embodiments, the expression of one or more of IFN-γ, IL-6, MCP-1, MIP-1β, IP-10, or TNF-α is increased by about 1.2-fold, 1.5-fold, 1.8-fold, 2-fold, 3-fold, 4-fold, 5-fold, 8-fold, or more than 10-fold in the conditioned plurality of modified PBMCs compared to an unconditioned plurality of modified PBMCs. In some embodiments, the expression of one or more of IFN-γ, IL-6, MCP-1, MIP-1β, IP-10, or TNF-α is increased by any of about 1.2-fold to about 1.5-fold, about 1.5-fold to about 1.8-fold, about 1.8-fold to about 2-fold, about 2-fold to about 3-fold, about 3-fold to about 4-fold, about 4-fold to about 5-fold, about 5-fold to about 8-fold, about 8-fold to about 10-fold, about 10-fold to about 20-fold, about 20-fold to about 50-fold, about 50-fold to about 100-fold, about 100-fold to about 200-fold, about 200-fold to about 500-fold, or more than about 500-fold in the conditioned plurality of modified PBMCs compared to an unconditioned plurality of modified PBMCs.

Systems and Kits

In some aspects, the invention provides a system comprising one or more of the constriction, a PBMC cell suspension, HPV antigens or adjuvants for use in the methods disclosed herein. The system can include any embodiment described for the methods disclosed above, including microfluidic channels or a surface having pores to provide cell-deforming constrictions, cell suspensions, cell perturbations, delivery parameters, compounds, and/or applications etc. In some embodiment, the cell-deforming constrictions are sized for delivery to PBMCs. In some embodiments, the delivery parameters, such as operating flow speeds, cell and compound concentration, velocity of the cell in the constriction, and the composition of the cell suspension (e.g., osmolarity, salt concentration, serum content, cell concentration, pH, etc.) are optimized for maximum response of a compound for suppressing an immune response or inducing tolerance.

Also provided are kits or articles of manufacture for use in treating individuals with a cancer associated with HPV. In some embodiments, the kit comprises PBMCs comprising intracellularly an HPV antigen and intracellularly an adjuvant. In some embodiments, the kit comprises one or more of the constriction, an PBMC suspension, HPV antigens or adjuvants for use in generating PBMCs for use in treating an individual with a disease associated with HPV, such as cancer. In some embodiments, the kits comprise the compositions described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for performing said methods treat an individual with a cancer associated with HPV and/or instructions for introducing at least one HPV antigen into PBMCs. The kits described herein may further include other materials, including other buffers, diluents, filters, needles, syringes, and package inserts with instructions for performing any methods described herein; e.g., instructions for treating an individual with a cancer associated with HPV or instructions for generating PBMCs to contain intracellularly at least one HPV antigen.

EXEMPLARY EMBODIMENTS

Embodiment 1. A pharmaceutical formulation comprising peripheral blood mononuclear cells (PBMCs), the formulation comprising
 a) PBMCs wherein the PBMCs comprise at least one antigen,
 b) a cryopreservation medium, and
 c) human serum albumin.

Embodiment 2. A pharmaceutical formulation comprising peripheral blood mononuclear cells (PBMCs), the formulation comprising
 a) PBMCs wherein the PBMCs comprise at least one antigen,
 b) a cryopreservation medium,
 c) a hypothermic preservation medium, and
 d) human serum albumin.

Embodiment 3. The formulation of claim 1 or 2, wherein the composition comprises about $5\times10^6$ PBMCs to about $5\times10^7$ PBMC.

Embodiment 4. The formulation of any one of claim 1 or 2, wherein the composition comprises about $2\times10^7$ PBMCs to about $3\times10^7$ PBMCs.

Embodiment 5. The formulation of any one of claims 1-4, wherein the composition comprises about $2.75\times10^7$ PBMCs.

Embodiment 6. The formulation of any one of claims 1-5, wherein the composition comprises about $1\times10^6$ PBMCs/mL to about $1\times10^7$ PBMC/mL.

Embodiment 7. The formulation of any one of claims 1-6, wherein the composition comprises about $4\times10^6$ PBMCs/mL to about $6\times10^6$ PBMCs/mL.

Embodiment 8. The formulation of any one of claims 1-7, wherein the composition comprises about $5.0\times10^6$ PBMCs/mL.

Embodiment 9. The formulation of any one of claims 1-8, wherein ≥70%, ≥80%, ≥90%, or ≥95% of the PBMCs in the composition are viable.

Embodiment 10. The formulation of any one of claims 1-6, the composition comprises about $3\times10^6$ viable PBMCs/mL to about $7\times10^6$ viable PBMCs/mL.

Embodiment 11. The formulation of any one of claims 1-6, wherein the composition comprises about $5\times10^6$ viable PBMCs/mL.

Embodiment 12. The formulation of any one of claims 1-11, wherein the composition had previously been frozen and the composition comprises about $4\times10^6$ viable PBMCs/mL after thawing.

Embodiment 13. The formulation of any one of claims 1-12, wherein the PBMCs in the formulation maintain about ≥70% viability following storage for at least 12 months at ≤−196° C.

Embodiment 14. The formulation of any one of claims 1-13, wherein the percentage of the cryopreservation medium in the formulation is about 40% to about 95% (w/w).

Embodiment 15. The formulation of any one of claims 1 and 3-14, wherein the percentage of the cryopreservation medium in the formulation is about 80% (w/w).

Embodiment 16. The formulation of any one of claims 2-14, wherein the percentage of the cryopreservation medium in the formulation is about 50% (w/w).

Embodiment 17. The formulation of any one of claims 1-16, wherein the cryopreservation medium comprises dimethylsulfoxide (DMSO).

Embodiment 18. The formulation of claim 17, wherein the percentage of DMSO is the cryopreservation medium is about 5% to about 15% (w/w).

Embodiment 19. The formulation of claim 17 or 18, wherein the percentage of DMSO is the cryopreservation medium is about 10% DMSO (w/w).

Embodiment 20. The formulation of any one of claims 1-19, wherein the cryopreservation medium is CryoStor® CS10.

Embodiment 21. The formulation of any one of claims 2-14 and 16-20, wherein the percentage of hypothermic preservation medium in the formulation is about 25% to about 35% (w/w).

Embodiment 22. The formulation of any one of claims 2-14 and 16-21, wherein the percentage of the hypothermic preservation medium in the formulation is about 30% (w/w).

Embodiment 23. The formulation of any one of claims 2-14 and 16-22, wherein the hypothermic preservation medium comprises a water soluble analog of vitamin E.

Embodiment 24. The formulation of any one of claims 2-14 and 16-23, wherein the hypothermic medium comprises trolox ((±)-6-hydroxy-2,5,7,8-tetramethylchromane-2-carboxylic acid).

Embodiment 25. The formulation of any one of claims 2-14 and 16-24, wherein the hypothermic preservation medium is HypoThermasol® FRS.

Embodiment 26. The formulation of any one of claims 1-25, wherein the human serum albumin is provided in a human serum albumin solution.

Embodiment 27. The formulation of claim 26, wherein the percentage of a human serum albumin solution in the formulation is about 15% to about 25% (w/w).

Embodiment 28. The formulation of claim 26 or 27, wherein the percentage of a human serum albumin solution in the formulation is about is about 20% (w/w).

Embodiment 29. The formulation of any one of claims 26-28, wherein the human serum albumin solution comprises sodium caprylate at a concentration of about 0.08 mmol/g of albumin and/or acetyltryptophan at a concentration of about 0.08 mmol/g albumin.

Embodiment 30. The formulation of any one of claims 1-29, wherein the percentage of a human serum albumin in the formulation is about is about 2% to about 8% (w/w).

Embodiment 31. The formulation of any one of claims 1-30, wherein the percentage of a human serum albumin in the formulation is about is about 5% (w/w). 10205 Embodiment 32. The formulation of any one of claims 1-31, wherein the pH of the formulation is about 6.0 to about 8.5.

Embodiment 33. The formulation of any one of claims 1-32, wherein the pH of the formulation is about 7.4.

Embodiment 34. A pharmaceutical formulation of peripheral blood mononuclear cells (PBMCs), the formulation comprising
 a) about $1\times10^6$ PBMCs/mL to about $1\times10^7$ PBMCs/mL, wherein PBMCs comprise at least one antigen,
 b) cryopreservation medium at a percentage of about 65% to about 95% (w/w), and
 c) human serum albumin about 2% to about 8%,
 wherein the pH of the formulation is about pH 6.0 to about pH 8.5.

Embodiment 35. A pharmaceutical formulation of peripheral blood mononuclear cells (PBMCs), the formulation comprising
 a) about $5\times10^6$ PBMCs/mL, wherein PBMCs comprise at least one antigen,
 b) cryopreservation medium at a percentage of about 50% (w/w), and
 c) human serum albumin at a percentage of about 5% (w/w),
 wherein the pH of the formulation is about pH 7.4.

Embodiment 36. A pharmaceutical formulation of peripheral blood mononuclear cells (PBMCs), the formulation comprising
a) about $1\times10^6$ PBMCs/mL to about $1\times10^7$ PBMCs/mL, wherein PBMCs comprise at least one antigen,
b) cryopreservation medium at a percentage of about 40% to about 60% (w/w),
c) hypothermic preservation medium at a percentage of about 25% to about 35%, and
d) human serum albumin about 2% to about 8%,
wherein the pH of the formulation is about pH 6.0 to about pH 8.5.

Embodiment 37. A pharmaceutical formulation of peripheral blood mononuclear cells (PBMCs), the formulation comprising
a) about $5\times10^6$ PBMCs/mL, wherein PBMCs comprise at least one antigen,
b) cryopreservation medium at a percentage of about 50% (w/w),
c) hypothermic preservation medium at a percentage of about 30% (w/w), and
d) human serum albumin at a percentage of about 5% (w/w),
wherein the pH of the formulation is about pH 7.4.

Embodiment 38. The formulation of claim 36 or 37, wherein the cryopreservation medium is CryoStor® CS10.

Embodiment 39. The formulation of any one of claims 36-38, wherein the hypothermic preservation medium is HypoThermasol® FRS.

Embodiment 40. The formulation of any one of claims 1-39, wherein the formulation is sterile.

Embodiment 41. The formulation of any one of claims 1-40, wherein the formulation comprises less than about 2 EU/mL endotoxin.

Embodiment 42. The formulation of any one of claims 1-41, wherein the formulation is free of mycoplasma.

Embodiment 43. The formulation of any one of claims 1-42, wherein the PBMCs comprises two or more of T cells, B cells, NK cells or monocytes.

Embodiment 44. The formulation of any one of claims 1-43, wherein the PBMCs comprises T cells, B cells, NK cells and monocytes.

Embodiment 45. The formulation of any one of claims 1-44, wherein
(a) about 25% to about 80% of the PBMCs are T cells;
(b) about 1.5% to about 30% of the PBMCs are B cells;
(c) about 3.0% to about 20% of the PBMCs are NK cells; or
(d) about 4.0% to about 45% of the PBMCs are monocytes.

Embodiment 46. The formulation of any one of claims 1-45, wherein the at least one antigen is a human papillomavirus (HPV) antigen.

Embodiment 47. The formulation of claim 46, wherein the HPV is HPV-16 or HPV-18.

Embodiment 48. The formulation of claim 46 or 47, wherein the at least one antigen comprises a peptide derived from HPV E6 and/or E7.

Embodiment 49. The formulation of any one of claims 46-48, wherein the at least one antigen comprises a peptide derived from HPV E6 and a peptide from HPV E7.

Embodiment 50. The formulation of any one of claims 46-49, wherein the at least one antigen comprises the amino acid sequence of any one of SEQ ID NOs:1-3.

Embodiment 51. The formulation of any one of claims 46-50, wherein the at least one antigen comprises the amino acid sequence of any one of SEQ ID NOs: 18-25.

Embodiment 52. The formulation of any one of claims 46-51, wherein the population of PBMCs comprises an antigen comprising the amino acid sequence of SEQ ID NO:19 and an antigen comprising the amino acid sequence of SEQ ID NO:23.

Embodiment 53. The formulation of any one of claims 1-52, wherein the PBMCs comprising the at least one antigen are prepared by a process comprising:
a) passing a cell suspension comprising a population of input PBMCs through a cell-deforming constriction, wherein a diameter of the constriction is a function of a diameter of the input PBMCs in the suspension, thereby causing perturbations of the input PBMCs large enough for the at least one antigen to pass through to form a population of perturbed input PBMCs; and
b) incubating the population of perturbed input PBMCs with the at least one antigen for a sufficient time to allow the antigen to enter the perturbed input PBMCs, thereby generating the population of PBMCs comprising the at least one antigen.

Embodiment 54. The formulation of claim 53, wherein the diameter of the constriction is about 4.2 µm to about 6 µm or about 4.2 µm to about 4.8 µm.

Embodiment 55. The formulation of any one of claims 1-54, wherein the PBMCs comprising the at least one antigen are conditioned.

Embodiment 56. The formulation of claim 55, wherein the population of PBMCs comprising the at least one antigen are conditioned by a process comprising incubating the PBMCs with the adjuvant for about 2 hours to about 10 hours, about 3 hours to about 6 hours, or about 4 hours at about 37° C. for the modified PBMCs to condition.

Embodiment 57. The formulation of claim 56, wherein the adjuvant is a CpG oligodeoxynucleotide (ODN), LPS, IFN-α, STING agonists, RIG-I agonists, poly I:C, R837, R848, a TLR3 agonist, a TLR4 agonist or a TLR 9 agonist.

Embodiment 58. The formulation of claim 47, wherein the adjuvant is a CpG 7909 oligodeoxynucleotide (ODN).

Embodiment 59. A vial comprising the formulation of any one of claims 1-58.

Embodiment 60. A vial comprising a formulation, the formulation comprising
a) about $5\times10^6$ PBMCs to about $5\times10^7$ PBMCs, wherein PBMCs comprise at least one antigen,
b) cryopreservation medium at a concentration of about 65% to about 95% (w/w), and
c) human serum albumin about 2% to about 8% (w/w),
wherein the pH of the formulation is about pH 6.0 to about pH 8.5.

Embodiment 61. A vial comprising a formulation, the formulation comprising
a) about $2.75\times10^7$ PBMCs, wherein PBMCs comprise at least one antigen,
b) cryopreservation medium at a concentration of about 80% (w/w), and
c) human serum albumin at a concentration of about 5%,
wherein the pH of the formulation is about pH 7.4.

Embodiment 62. A vial comprising a formulation, the formulation comprising
a) about $1\times10^6$ PBMCs/mL to about $1\times10^7$ PBMCs/mL, wherein PBMCs comprise at least one antigen,
b) cryopreservation medium at a concentration of about 40% to about 60% (w/w),
c) hypothermic preservation medium about 25% to about 35% (w/w), and d) human serum albumin about 2% to about 8%,
wherein the pH of the formulation is about pH 6.0 to about pH 8.5.

Embodiment 63. A vial comprising a formulation, the formulation comprising
  a) about $5\times10^6$ PBMCs/mL, wherein PBMCs comprise at least one antigen,
  b) cryopreservation medium at a concentration of about 50% (w/w),
  c) hypothermic preservation medium at a concentration of about 30% (w/w), and
  d) human serum albumin at a concentration of about 5% (w/w),
wherein the pH of the formulation is about pH 7.4.

Embodiment 64. The vial of any one of claims 60-63, wherein the cryopreservation medium is CryoStor® CS10.

Embodiment 65. The vial of any one of claims 62-64, wherein the hypothermic preservation medium is HypoThermasol® FRS.

Embodiment 66. The vial of any one of claims 59-65, wherein the formulation is sterile.

Embodiment 67. A method of producing a formulation of PBMCs, the method comprising adding a cryopreservation medium and human serum albumin to a population of PBMCs wherein the PBMCs comprise at least one antigen.

Embodiment 68. The method of claim 67, wherein
  a) the population of PBMCs in the formulation is about $1\times10^6$ PBMCs/mL to about $1\times10^7$ PBMCs/mL,
  b) the cryopreservation medium is added to a percentage of about 65% to about 95% (w/w), and
  c) the human serum albumin is added to a concentration of about 2% to about 8% (w/w),
wherein the pH of the formulation is adjusted to about pH 6.0 to about pH 8.5.

Embodiment 69. The method of claim 68, wherein
  a) the population of PBMCs in the formulation is about $6\times10^6$ PBMCs,
  b) the cryopreservation medium is added to a percentage of about 80% (w/w), and
  c) the human serum albumin is added to a percentage of about 5% (w/w),
wherein the pH of the formulation is adjusted to about pH 7.4.

Embodiment 70. A method of producing a formulation of PBMCs, the method comprising adding a cryopreservation medium, a hypothermic preservation medium, and human serum albumin solution to a population of PBMCs wherein the PBMCs comprise an antigen.

Embodiment 71. The method of claim 70, wherein
  a) the population of PBMCs in the formulation is about $1\times10^6$ PBMCs to about $1\times10^7$ PBMCs,
  b) the cryopreservation medium is added to a percentage of about 40% to about 60% (w/w),
  c) the hypothermic preservation medium is added to a percentage of about 25% to about 35% (w/w), and
  d) the human serum albumin solution is added to a percentage of about 15% to about 25% (w/w),
wherein the pH of the formulation is adjusted to about pH 6.0 to about pH 8.5.

Embodiment 72. The method of claim 70 or 71, wherein
  a) the population of PBMCs in the formulation is about $6\times10^6$ PBMCs,
  b) the cryopreservation medium is added to a percentage of about 50% (w/w),
  c) the hypothermic preservation medium is added to a percentage of about 30% (w/w), and
  d) the human serum albumin is added to a percentage of about 20% (w/w),
wherein the pH of the formulation is adjusted to about pH 7.4.

Embodiment 73. The method of any one of claims 67-72, wherein the cryopreservation medium is CryoStor® CS10.

Embodiment 74. The method of any one of claims 70-73, wherein the hypothermic preservation medium is HypoThermasol® FRS.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1. Development of SQZ-PBMC-HPV

PBMC-HPV drug substance consists of autologous PBMCs presenting HLA-A*02 restricted E6 and E7 epitopes of HPV16 on major histocompatibility complex Class I (MHC-I). The majority of PBMCs (>90%) consist of T cells, monocytes, NK cells, and B cells.

E6 SLP and E7 SLP used as starting materials in the production of PBMC-HPV drug substance are shown below. These peptides contain antigenic epitopes for HPV16 (shown in bold letters).
  E6 SLP: QLCTELQTTIHDIILECVYCKQQLL (SEQ ID NO:19)
  E7 SLP: QLCTELQTYMLDLQPETTYCKQQLL (SEQ ID NO:23)

After being delivered into the cell cytosol during the manufacturing process, these peptides are processed by the cells and the resultant segments containing antigenic epitopes are presented on the MHC-I of the various PBMC cells.

As part of the PBMC-HPV drug substance manufacturing process, the PBMC-HPV cells are matured (or conditioned) with CpG 7909, a CpG oligodeoxynucleotide (ODN). This maturation results in production of inflammatory cytokines by PBMC-HPV cells and upregulation of costimulatory molecules (e.g., CD86) and MHC-I on B cells. After the maturation period, the PBMC-HPV drug substance is washed twice and subsequently formulated into the drug product, SQZ PBMC HPV.

All studies performed to develop the PBMC-HPV drug substance process were executed using healthy donor leukopak material, PBMC Purification Elutriation is the process used for purification of PBMCs from the leukopak. Recommendations for use of key elutriation process parameters, choice of elutriation media (Hank's Balanced Salt Solution (HBSS) with 1% Human Serum Albumin (HSA)), and dilution of starting material were provided by the equipment vendor (Terumo BCT).

Peptide (E6 and E7 SLPs) Introduction

Following elutriation, purified PBMCs are washed twice with Gibco™ RPMI 1640 Medium and subsequently resuspended with delivery media (a solution of 50 μM E6 and 50 μM E7 in Gibco™ RPMI 1640 Medium) using the LOVO system. Processing parameters used on the LOVO system for washing and formulating PBMCs with delivery media were provided by the equipment vendor (Fresenius Kabi).

Peptide (E6 and E7 SLPs) Delivery

Following the resuspension of PBMCs with the delivery media, the combined mixture is cooled to 2-8° C. using the SQZ system, and subsequently flowed through two parallel silicon microfluidic chips, with the cells collected in a sterile single use bag containing quench media (Gibco™ RPMI 1640 Medium and 10% Human Serum).

PBMC Maturation with CpG 7909

Following delivery of the E6 and E7 SLPs into the PBMCs, a sterile filtered solution of CpG 7909 formulated in PBS at a concentration of 0.35 mg/mL is aseptically added to the cell suspension, and the cells are matured for four hours at 37° C.±1° C. resulting in the PBMC-HPV drug substance.

Cell recovery for each unit operation was calculated across five process development lots (Table 1).

TABLE 1

Cell Recover per Unit Operation

| Experiment # | PBMC Purification | Peptide Introduction | Peptide Delivery | PBMC Maturation with CpG 7909 | Cumulative Drug Substance Process Recovery |
|---|---|---|---|---|---|
| 1 | 103% | 88% | 77% | 76% | 53% |
| 2 | 96% | 105% | 65% | 78% | 51% |
| 3 | 105% | 91% | 85% | 66% | 54% |
| 4 | 108% | 108% | 73% | 63% | 54% |
| 5 | 90% | 91% | 95% | 78% | 61% |
| Mean | 100% | 97% | 79% | 72% | 54% |
| STDEV | 7% | 9% | 12% | 7% | 4% |
| Min | 90% | 88% | 65% | 63% | 51% |
| Max | 108% | 108% | 95% | 78% | 61% |

Based on the average process recovery from leukopak to drug product (30.1%), one would estimate the proposed minimum WBCs in the leukopak, $4\times10^9$ total, would yield 43 vials ($4\times10^9 \times 30.1\%/2.75\times10^7$ cells/vial).

Example 2. Development of PBMC-HPV Formulation

SQZ-PBMC-HPV consists of formulated PBMC-HPV drug substance, autologous antigen presenting PBMCs targeting the immunogenic epitopes of the E6 and E7 proteins of the human papillomavirus 16 (HPV16). The PBMCs consist primarily of monocytes, T cells, B cells and NK cells.

SQZ-PBMC-HPV is prepared by formulating PBMC-HPV drug substance in a solution containing 50% (w/w) of CryoStor® CS10, 30% (w/w) of HypoThermosol® FRS, and 20% (w/w) of 25% Human Serum Albumin to a concentration of $5\times10^6$ live cells/mL, and filling into vials. The vials are cryopreserved using a chamber temperature of ≤−170° C., with the vials reaching and maintaining a temperature of ≤−140° C. during production, storage and shipment.

For the development of SQZ-PBMC-HPV formulation, an evaluation of CryoStor® base medium at different DMSO concentrations (5, 7.5, and 10%) was completed. Live cells were formulated into each cryomedia formulation, aliquoted into cryovials, and frozen using a controlled rate freezer to a chamber temperature of ≤−170° C. Post thaw, each formulation was assessed for cell count and viability. A final DMSO concentration of 5% exhibited the highest live cell recovery and viability post-thaw among the conditions tested and was selected as the final concentration for the drug product formulation.

To optimize for cell recovery and viability post thaw, human serum albumin (HSA) was incorporated with the CryoStor® base media (final DMSO concentration of 5%) at different concentrations (0, 5, and 10%). Cells were then combined through resuspension into each media formulation, aliquoted into cryovials, and frozen using a controlled rate freezer to a chamber temperature of ≤−170° C. Post thaw, each formulation was assessed for cell count and viability and a final HSA concentration of 5% was deemed optimal for SQZ-PBMC-HPV. Based on these evaluations, a final drug product formulation containing 5% DMSO and 5% HSA was chosen for SQZ-PBMC-HPV.

Preceding the final drug product formulation, the PBMC-HPV drug substance was washed twice with the formulation media, and then resuspended in the same media. Processing parameters used on the LOVO system for washing the PBMC-HPV drug substance and subsequently formulating SQZ-PBMC-HPV were provided by the equipment vendor (Fresenius Kabi).

Vial filling is performed inside an ISO 5 biosafety cabinet. Vials are supplied sterile, fully stoppered and ready to use. For filling, each vial is filled with 5.78 g±5% of product (a critical process parameter, ie, 5.5 mL, which allows for a delivered volume of 5 mL). Following filling, each vial is sealed, checked for weight, and subsequently capped. Once vial filling is completed, each filled vial is visually inspected for any visible defects (including particulate matter) using an inspection booth equipped with an illuminated black and white background. Subsequently, each vial is labeled with a cryogenic label.

After labeling, all vials are loaded into a controlled rate freezer and the final drug product is cryopreserved using a chamber temperature of ≤−170° C., with the vials reaching a temperature of ≤−140° C. (a critical process parameter). The Tg of the cryopreservation media is −120 to −130° C. The cryopreserved vials are placed in an isothermal $LN_2$ tank for long term storage.

The cryopreservation profile protocol that was developed in shown in Table 2.

TABLE 2

Cryopreservation Protocol

| Step | Parameter |
|---|---|
| 1 | Decrease chamber temperature by −2° C./min to 0° C. |
| 2 | Hold chamber at 0° C. for 5 minutes |
| 3 | Decrease product temperature by −1° C./min to −3° C. |
| 4 | Decrease chamber temperature by −15° C./min to −100° C. |
| 5 | Hold chamber at −100° C. for 5 minutes |
| 6 | Decrease product temperature by −3° C./min to −150° C. |
| 7 | Decrease chamber temperature by −2° C./min to −170° C. |
| 8 | Hold chamber at −170° C. for 5 minutes |
| 9 | End profile |

A set of batches with leukopaks from healthy subjects were produced to ensure consistency. The data generated from the batches are shown in Table 3.

TABLE 3

Characterization of batches

| Batch | Leukopak Cell Count (WBCs) | Leukopak Viability | Drug Product Batch Size | Drug Product Vials Filled[a] | Post-Thaw Total Cell Concentration | Post-Thaw Cell Viability | Overall Process Recovery[a] |
|---|---|---|---|---|---|---|---|
| 1 | $15.5 \times 10^9$ | 98.4% | 397 g | 71 | $5.9 \times 10^6$ cells/mL | 86.3% | 14.9% |
| 2 | $13.6 \times 10^9$ | 98.9% | 885 g | 160 | $4.6 \times 10^6$ cells/mL | 90.2% | 29.8% |
| 3 | $9.3 \times 10^9$ | 99.0% | 678 g | 123 | $6.0 \times 10^6$ cells/mL | 92.7% | 43.3% |
| 4 | $12.1 \times 10^9$ | 97.3% | 786 g | 137 | $4.8 \times 10^6$ cells/mL | 91.5% | 24.7% |
| 5 | $6.2 \times 10^9$ | 98.2% | 416 g | 73 | $5.8 \times 10^6$ cells/mL | 90.6% | 37.6% |
| Mean | $11.4 \times 10^9$ | 98.4% | 632 g | 112 | $5.4 \times 10^6$ cells/mL | 90.3% | 30.0% |
| Range | $6.2 \times 10^9$–$15.5 \times 10^9$ | 97.3–99.0% | 397–885 g | 71–160 | $4.6 \times 10^6$–$6.0 \times 10^6$ cells/mL | 86.3–92.7% | 14.9–43.3% |

Stability

A summary of the long-term stability studies for SQZ-PBMC-HPV drug product is presented in Table 4. Sterility testing and endotoxin testing were performed at release of each batch. In lieu of testing the drug product for mycoplasma, in-process wash samples generated during the manufacture of the drug product were tested for mycoplasma. Testing of these wash samples is more sensitive for detecting mycoplasma than testing of the final drug product.

TABLE 4

Stability

| | | Long-Term Stability Results (N = 5 Batches) | | |
|---|---|---|---|---|
| Test | Current Criteria | Last Point Analyzed | Range of Results T = 0 | Range of Results Post T = 0 |
| Appearance | Off white, yellow or pink cell suspension free of foreign particulates | 3 Months[a] | Yellow or pink cell suspension free of foreign particulates | Yellow or pink cell suspension free of foreign particulates |
| ID (Phenotype) | Positive for main cell type surface marker CD45 | | Positive | Positive |
| Composition Frequency (%) | ≥90% CD45+ cells | | 98.7–99.9 | 99.2–99.9 |
| Dose - Total Cell Count (cells/mL) | Report | | $4.60 \times 10^6$–$5.95 \times 10^6$ | $4.23 \times 10^6$–$6.63 \times 10^6$ |
| Dose - Viability % | ≥70 | | 86.3–92.7 | 88.1–93.4 |
| pH | 6.0–8.5 | | 7.4–7.5 | 7.4–7.5 |
| Endotoxin (EU/mL) | ≤2 | | <1 | NA |
| IFNγ Secretion (pg/mL) | Not Applicable, Characterization Test | | 376–1834 | 499–3726 |

NA = not applicable

[a]Data are available for T = 0 and 1 month for all 5 batches, 2 months for 3 batches aid 3 months for 2 batches.

SEQUENCES

| SEQ ID NO | Sequence | Description |
|---|---|---|
| 1 | TIHDIILECV | HPV16-E6(29-38), human epitope |
| 2 | EVYDFAFRDL | HPV16-E6(48-57), murine epitope |
| 3 | YMLDLQPETT | HPV16-E7(11-20), human epitope |
| 4 | RAHYNIVTF | HPV16-E7(49-57), murine epitope |

-continued

| SEQ ID NO | Sequence | Description |
|---|---|---|
| 5 | LPQLSTELQT | HPV16-E6(19-28) N-terminal polypeptide, human |
| 6 | QLCTELQT | HPV16-E6(21-28) N-terminal polypeptide, human |
| 7 | KQQLLRR | HPV16-E6(41-47) N-terminal polypeptide, native murine |
| 8 | VYSKQQLLRR | HPV16-E6(38-47) N-terminal polypeptide, classic murine |
| 9 | MHGDTPTLHE | HPV16-E7(1-10) N-terminal polypeptide, human |
| 10 | GQAEPD | HPV16-E7(43-48) N-terminal polypeptide, murine |
| 11 | YSKQQLLRREVYDFAF | HPV16-E6(39-54) C-terminal polypeptide, human |
| 12 | YCKQQLL | HPV16-E6(39-45) C-terminal polypeptide, human |
| 13 | CIVYRDGN | HPV16-E6(58-65) C-terminal polypeptide, native murine |
| 14 | SIVYRDGNPYAVSDK | HPV16-E6(58-72) C-terminal polypeptide, classic murine |
| 15 | DLYCYEQLNDSSEEE | HPV16-E7(21-35) C-terminal polypeptide, human |
| 16 | CCKCDSTLRLCVQSTHVDIR | HPV16-E7(58-77 C-terminal polypeptide, native murine |
| 17 | SSKSDSTLRLSVQSTHVDIR | HPV16-E7(58-77) C-terminal polypeptide, classic murine |
| 18 | LPQLSTELQTTIHDIILECVYSKQQLLRREVYDFAF | HPV16-E6(19-54) SLP, human |
| 19 | QLCTELQTTIHDIILECVYCKQQLL | HPV16-E6(21-45) SLP, human |
| 20 | KQQLLRREVYDFAFRDLCIVYRDGN | HPV16-E6(41-65) SLP, native murine |
| 21 | VYSKQQLLRREVYDFAFRDLSIVYRDGNPYAVSDK | HPV16-E6(38-72) SLP, classic murine |
| 22 | MHGDTPTLHEYMLDLQPETTDLYCYEQLNDSSEEE | HPV16-E7(1-35) SLP, human |
| 23 | QLCTELQTYMLDLQPETTYCKQQLL | HPV16-E7.6 SLP, human |
| 24 | GQAEPDRAHYNIVTFCCKCDSTLRLCVQSTHVDIR | HPV16-E7(43-77) SLP, native murine |
| 25 | GQAEPDRAHYNIVTFSSKSDSTLRLSVQSTHVDIR | HPV16-E7(43-77) SLP, classic murine |
| 26 | ggGGTCAACGTTGAgggggg<br>Bases shown in capital letters are phosphodiester, and those in lower case are phosphorothioate | ODN 1585 (Class A, mouse-specific) |
| 27 | ggGGGACGA:TCGTCgggggg<br>Bases shown in capital letters are phosphodiester, and those in lower case are phosphorothioate | ODN 2216 (Class A, human-selective) |

| SEQ ID NO | Sequence | Description |
|---|---|---|
| 28 | gggGACGAC:GTCGTGgggggg<br>Bases shown in capital letters are phosphodiester, and those in lower case are phosphorothioate | ODN 2336 (Class A, human preferred) |
| 29 | tccatgacgttcctgatgct<br>Bases shown in capital letters are phosphodiester, and those in lower case are phosphorothioate | ODN 1668 (Class B, mouse specific) |
| 30 | tccatgacgttcctgacgtt<br>Bases are phosphorothioate | ODN 1826 (Class B, mouse specific) |
| 31 | tcgtcgttttgtcgttttgtcgtt<br>Bases are phosphorothioate | ODN 2006 (Class B, human selective) |
| 32 | tcg tcg ttg tcg ttt tgt cgt t<br>Bases are phosphorothioate | ODN 2007 (Class B, bovine/porcine) |
| 33 | tcg acg ttc gtc gtt cgt cgt tc<br>Bases are phosphorothioate | ODN BW006 (Class B, human & mouse) |
| 34 | tcg cga cgt tcg ccc gac gtt cgg ta<br>Bases are phosphorothioate | ODN D-SL01 (Class B, multispecies) |
| 35 | tcgtcgttttcggcgc:gcgccg<br>Bases are phosphorothioate | ODN 2395 (Class C, human/mouse) |
| 36 | tcgtcgtcgttc:gaacgacgttgat<br>Bases are phosphorothioate | ODN M362 (Class C, human/mouse) |
| 37 | tcg cga acg ttc gcc gcg ttc gaa cgc gg<br>Bases are phosphorothioate | ODN D-SL03 (Class C, multispecies) |
| 38 | MHGDTPTLHEYMLDLQPETTDLYCYEQLNDSSEEE | E7 |
| 39 | LYCYEQLNDSSEEEDEIDGPAGQAEPDRAHYNIVT | E7 |
| 40 | GQAEPDRAHYNIVTFCCKCDSTLRLCVQSTHVDIR | E7 |
| 41 | TLRLCVQSTHVDIRTLEDLLMGTLGIVCPICSQKP | E7 |
| 42 | MHQKRTAMFQDPQERPRKLPQLCTELQTTIHD | E6 |
| 43 | LPQLCTELQTTIHDIILECVYCKQQLLRREVY | E6 |
| 44 | KQQLLRREVYDFAFRDLCIVYRDGN | E6 |
| 45 | RDLCIVYRDGNPYAVCDKCLKFYSKI | E6 |
| 46 | DKCLKFYSKISEYRHYCYSLYGTTL | E6 |
| 47 | HYCYSLYGTTLEQQYNKPLCDLLIR | E6 |
| 48 | YGTTLEQQYNKPLCDLLIRCINCQKPLCPEEK | E6 |
| 49 | RCINCQKPLCPEEKQRHLDKKQRFHNIRGRWT | E6 |
| 50 | DKKQRFHNIRGRWTGRCMSCCRSSRTRRETQL | E6 |

What is claimed is:

1. A pharmaceutical formulation comprising:
   a) peripheral blood mononuclear cells (PBMCs), which comprise at least one antigen,
   b) a cryopreservation medium,
   c) a hypothermic preservation medium, which is present at a percentage of about 25% to about 35% (w/w), and
   d) human serum albumin.

2. The pharmaceutical formulation of claim 1, which comprises: (i) about $5 \times 10^6$ PBMCs to about $5 \times 10^7$ PBMCs; or (ii) about $1 \times 10^6$ PBMCs/mL to about $1 \times 10^7$ PBMC/mL.

3. The pharmaceutical formulation of claim 1, wherein the cryopreservation medium is present in the formulation at a percentage of about 40% to about 95% (w/w).

4. The pharmaceutical formulation of claim 1, wherein the hypothermic preservation medium comprises: (i) a water-soluble analog of vitamin E; (ii) trolox ((±)-6-hydroxy-2,5,7,8-tetramethylchromane-2-carboxylic acid); or (iii) both (i) and (ii).

5. The pharmaceutical formulation of claim 1, wherein the human serum albumin: (i) is present in the formulation at a percentage of about 2% to about 8% (w/w) or (ii) is provided in a human serum albumin solution at a percentage of about 15% to about 25% (w/w).

6. The pharmaceutical formulation of claim 1, wherein the pH of the formulation is about 6.0 to about 8.5.

7. The pharmaceutical formulation of claim 1, which comprises:

a) about $1\times10^6$ PBMCs/mL to about $1\times10^7$ PBMCs/mL,
b) the cryopreservation medium at a percentage of about 65% to about 95% (w/w), and
c) the human serum albumin at a percentage of about 2% to about 8% (w/w),
wherein the pH of the formulation is about pH 6.0 to about pH 8.5.

8. The pharmaceutical formulation of claim 1, which comprises:
a) about $1\times10^6$ PBMCs/mL to about $1\times10^7$ PBMCs/mL,
b) the cryopreservation medium at a percentage of about 40% to about 60% (w/w), and
c) the human serum albumin at a percentage of about 2% to about 8% (w/w), and
wherein the pH of the formulation is about pH 6.0 to about pH 8.5.

9. The pharmaceutical formulation of claim 1, wherein the PBMCs comprise T cells, B cells, NK cells, monocytes, or combinations thereof.

10. The pharmaceutical formulation of claim 1, wherein the at least one antigen comprises one or more human papillomavirus (HPV) antigens.

11. The pharmaceutical formulation of claim 10, wherein the one or more HPV antigens comprise the amino acid sequence of any one of SEQ ID NOs: 1-4 and 18-25.

12. The pharmaceutical formulation of claim 1, wherein the PBMCs have been conditioned with an adjuvant.

13. The pharmaceutical formulation of claim 12, wherein the adjuvant comprises a CpG oligodeoxynucleotide (ODN), LPS, IFN-α, a STING agonist, a RIG-I agonist, poly I:C, R837, R848, a TLR3 agonist, a TLR4 agonist, a TLR 9 agonist, or a combination thereof.

14. A vial comprising the pharmaceutical formulation of claim 1.

15. A method of producing a pharmaceutical formulation comprising PBMCs, the method comprising adding a cryopreservation medium, a hypothermic preservation medium, and human serum albumin to a population of PBMCs to produce the formulation, wherein the PBMCs comprise at least one antigen, and wherein the hypothermic preservation medium is added to a percentage of about 25% to about 35% (w/w).

16. The method of claim 15, wherein
a) the population of PBMCs in the formulation is about $1\times10^6$ PBMCs to about $1\times10^7$ PBMCs,
b) the cryopreservation medium is added to a percentage of about 40% to about 60% (w/w), and/or
c) the human serum albumin solution is added to a percentage of about 15% to about 25% (w/w), and
wherein the pH of the formulation is adjusted to about pH 6.0 to about pH 8.5.

17. The method of claim 15, further comprising:
(a) passing a cell suspension comprising a population of input PBMCs through a cell-deforming constriction, thereby causing perturbations of the input PBMCs; and
(b) contacting the population of perturbed input PBMCs with the at least one antigen such that the at least one antigen passes through the perturbations and enters the perturbed input PBMCs to generate the population of PBMCs comprising the at least one antigen.

18. A method of treating a disease or disorder in a subject in need thereof, comprising administering to the subject the pharmaceutical formulation of claim 1.

* * * * *